United States Patent
Adachi et al.

(10) Patent No.: US 9,215,533 B2
(45) Date of Patent: Dec. 15, 2015

(54) UNCOMFORTABLE SOUND PRESSURE DETERMINATION SYSTEM, METHOD AND PROGRAM THEREOF, HEARING AID ADJUSTMENT SYSTEM, AND UNCOMFORTABLE SOUND PRESSURE DETERMINATION APPARATUS

(71) Applicant: Panasonic Corporation, Osaka (JP)

(72) Inventors: Shinobu Adachi, Nara (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 349 days.

(21) Appl. No.: 13/788,806

(22) Filed: Mar. 7, 2013

(65) Prior Publication Data

US 2013/0182860 A1 Jul. 18, 2013

Related U.S. Application Data

(63) Continuation of application No. PCT/JP2012/004244, filed on Jun. 29, 2012.

(30) Foreign Application Priority Data

Jun. 30, 2011 (JP) .................................. 2011-146093

(51) Int. Cl.
*H04R 29/00* (2006.01)
*H04R 25/00* (2006.01)
(Continued)

(52) U.S. Cl.
CPC ............ *H04R 25/30* (2013.01); *A61B 5/04845* (2013.01); *A61B 5/125* (2013.01);
(Continued)

(58) Field of Classification Search
CPC .......... H04R 25/00; H04R 9/00; H04R 23/00; H04R 25/30; H04R 25/70; A61B 5/6815; A61B 5/6803; A61B 5/04845; A61B 5/125
USPC ...................................... 381/60, 312; 607/55
See application file for complete search history.

(56) References Cited

U.S. PATENT DOCUMENTS

2001/0049480 A1 12/2001 John et al.
2004/0064066 A1 4/2004 John et al.
(Continued)

FOREIGN PATENT DOCUMENTS

JP 2004-179965 A 6/2004
JP 2009-288354 A 12/2009
(Continued)

OTHER PUBLICATIONS

International Search Report for corresponding International Application No. PCT/JP2012/004244 mailed Sep. 11, 2012.
(Continued)

*Primary Examiner* — Matthew Eason
*Assistant Examiner* — Sean H Nguyen
(74) *Attorney, Agent, or Firm* — Renner, Otto, Boisselle & Sklar, LLP

(57) ABSTRACT

An exemplary uncomfortable sound pressure determination system including: a sound data generator configured to generate sound data concerning sounds consecutively ascending or descending in sound pressure from first to $n^{th}$ sounds, the sounds being pure tones of a same frequency; an output section configured to present the sounds to a user; a characteristic amount extractor configured to extract, based on an event-related potential of the electroencephalogram signal measured after lapse of a predetermined time from a point in time of presenting each of the sounds, a characteristic amount concerning temporal change in frequency of the event-related potential; and an uncomfortable sound pressure determination section configured to determine, by referring to a previously-provided relationship by which temporal changes in frequency of event-related potentials and uncomfortable sound pressures are associated, a sound pressure corresponding to the extracted characteristic amount to be an uncomfortable sound pressure at the frequency.

18 Claims, 12 Drawing Sheets

(51) Int. Cl.
*A61B 5/0484* (2006.01)
*A61B 5/12* (2006.01)
*H04R 23/00* (2006.01)
*H04R 9/00* (2006.01)
*A61B 5/00* (2006.01)

(52) U.S. Cl.
CPC ............ *A61B 5/6803* (2013.01); *A61B 5/6815* (2013.01); *H04R 9/00* (2013.01); *H04R 23/00* (2013.01); *H04R 25/00* (2013.01); *H04R 25/70* (2013.01)

(56) References Cited

U.S. PATENT DOCUMENTS

| | | |
|---|---|---|
| 2004/0204659 A1 | 10/2004 | John et al. |
| 2005/0043646 A1* | 2/2005 | Viirre et al. .......... A61B 5/0482 600/545 |
| 2006/0036297 A1* | 2/2006 | Seidman ................ A61N 1/361 607/55 |
| 2009/0163828 A1* | 6/2009 | Turner et al. ................... 600/559 |
| 2012/0283593 A1* | 11/2012 | Searchfield et al. .......... 600/559 |

FOREIGN PATENT DOCUMENTS

| | | |
|---|---|---|
| WO | 01/87147 A2 | 11/2001 |
| WO | 2008/038650 A1 | 4/2008 |

OTHER PUBLICATIONS

Kimitsuki et al., "Inner ear auditory testing in patients with normal hearing showing hyperacusis", Audiology Japan 52, pp. 152-156, 2009 and concise explanation.

Thornton et al., "The objective estimation of loudness discomfort level using auditory brainstem evoked responses", Sc and Audiol.; 16(4):219-25 1987 (Abstract).

Jishoukandrendeni (ERP) Manyuaru-P300 WO Chushinni-(or "Event-Related Potential (ERP) Manual—mainly concerning P300-"), edited by Kimitaka Kaga et al., Shinohara Shuppan Shinsha, 1995, p. 30 and concise explanation.

Co-pending U.S. Appl. No. 13/909,421 filed Jun. 4, 2013.

* cited by examiner

|  | RIGHT | | | LEFT | | |
|---|---|---|---|---|---|---|
|  | 1000 Hz | 2000 Hz | 4000 Hz | 1000 Hz | 2000 Hz | 4000 Hz |
| PARTICIPANT 01 | 87.5 | 97.5 | 92.5 | 92.5 | 100 | 90 |
| PARTICIPANT 02 | 97.5 | 97.5 | 90 | 100 | 100 | 90 |
| PARTICIPANT 03 | 110 | 102.5 | 97.5 | 110 | 97.5 | 110 |
| PARTICIPANT 04 | 82.5 | 82.5 | 72.5 | 82.5 | 82.5 | 82.5 |
| PARTICIPANT 05 | 90 | 85 | 80 | 85 | 87.5 | 87.5 |
| PARTICIPANT 06 | 80 | 87.5 | 92.5 | 92.5 | 95 | 100 |
| PARTICIPANT 07 | 95 | 95 | 90 | 95 | 95 | 85 |
| PARTICIPANT 08 | 100 | 97.5 | 90 | 97.5 | 97.5 | 95 |
| PARTICIPANT 09 | 92.5 | 95 | 95 | 97.5 | 97.5 | 97.5 |
| PARTICIPANT 10 | 77.5 | 82.5 | 77.5 | 75 | 72.5 | 80 |
| PARTICIPANT 11 | 105 | 97.5 | 97.5 | 100 | 97.5 | 95 |
| PARTICIPANT 12 | 97.5 | 100 | 92.5 | 100 | 100 | 100 |
| AVERAGE | 92.9 | 93.3 | 89.0 | 94.0 | 93.5 | 92.7 |
| STANDARD DEVIATION | 9.5 | 6.7 | 7.7 | 9.0 | 8.1 | 8.2 |

UPPER VIEW    FRONTAL VIEW

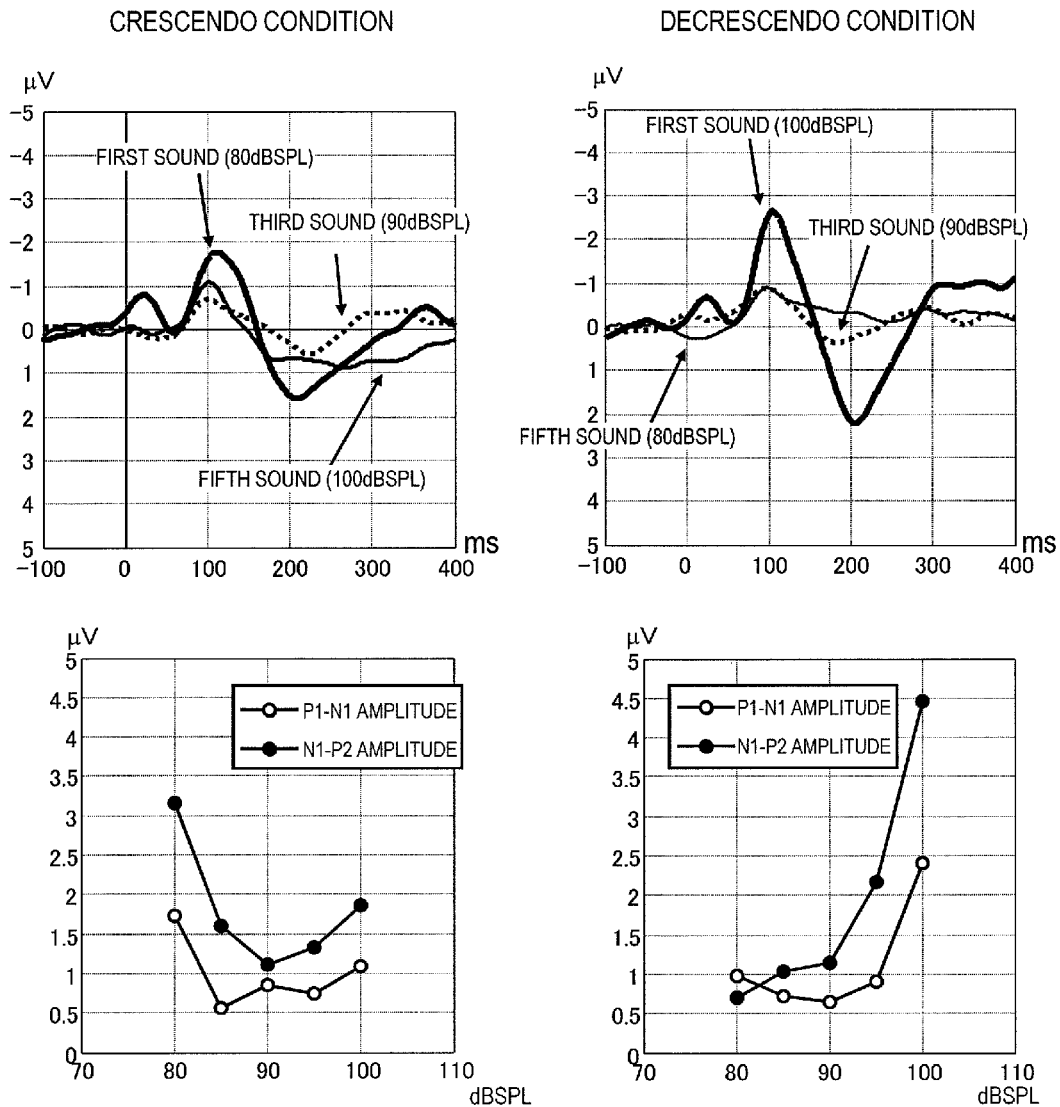

FIG.5
(a)
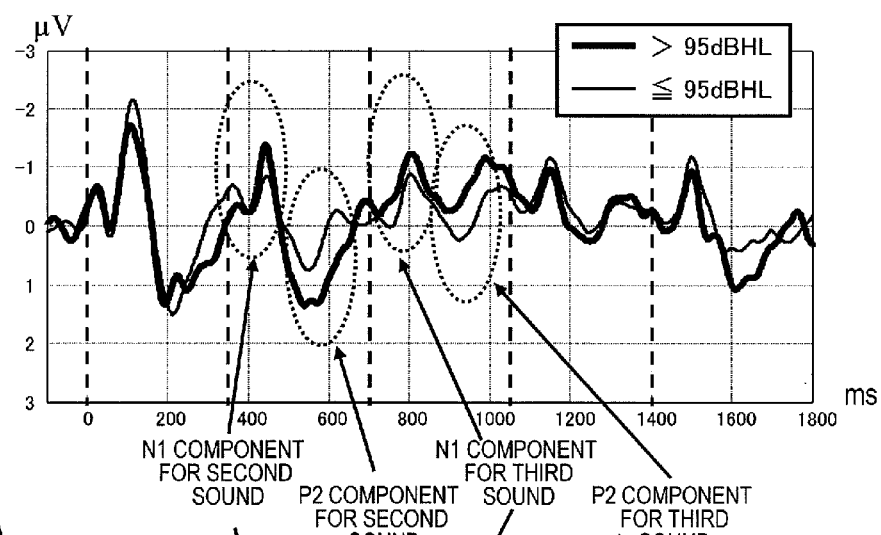
(b)
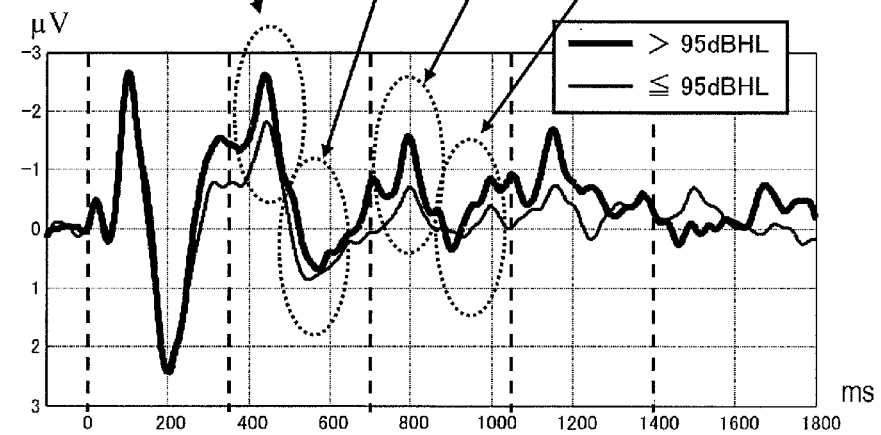

FIG.8

| PARTIC-IPANT | SOUND STIMULATION GROUP | | SUBJECTIVE UCL VALUE | FIRST SOUND | SECOND SOUND | THIRD SOUND | FOURTH SOUND | FIFTH SOUND |
|---|---|---|---|---|---|---|---|---|
| | RIGHT/LEFT | FREQUENCY | | | | | | |
| 01 | RIGHT | 1000Hz | 87.5 | 1.72 | −0.19 | −0.48 | 0.45 | −0.05 |
| | | 2000Hz | 97.5 | 1.45 | −0.70 | 1.44 | 2.62 | 1.81 |
| | | 4000Hz | 92.5 | 0.79 | 1.14 | −2.11 | 0.48 | 4.10 |
| | LEFT | 1000Hz | 92.5 | −0.58 | 1.23 | 1.07 | 0.06 | 1.78 |
| | | 2000Hz | 100 | 0.65 | −0.91 | −1.73 | 1.34 | 0.36 |
| | | 4000Hz | 90 | −0.70 | 0.21 | 0.58 | −0.21 | −1.24 |
| 02 | RIGHT | 1000Hz | 97.5 | −0.85 | 1.39 | 0.68 | −0.32 | 3.74 |
| | | 2000Hz | 97.5 | 1.17 | −0.43 | 0.09 | 0.19 | 0.43 |
| | | 4000Hz | 90 | 1.33 | 0.09 | −0.66 | 0.02 | 1.23 |
| | LEFT | 1000Hz | 100 | −1.16 | 0.98 | −0.44 | −0.10 | 3.46 |
| | | 2000Hz | 100 | −1.27 | −0.55 | −0.69 | 1.99 | 1.62 |
| | | 4000Hz | 90 | −0.11 | 0.47 | −0.62 | 0.01 | 2.09 |
| 03 | RIGHT | 1000Hz | 110 | 1.96 | −0.29 | 0.28 | −0.23 | 0.82 |
| | | 2000Hz | 102.5 | 0.86 | 1.00 | 1.89 | 2.25 | 0.87 |
| | | 4000Hz | 97.5 | −1.23 | 0.50 | 0.61 | −0.20 | 2.06 |
| | LEFT | 1000Hz | 110 | 1.01 | −0.21 | −0.14 | −0.62 | −0.04 |
| | | 2000Hz | 97.5 | 1.08 | −1.26 | 0.96 | 1.53 | 1.50 |
| | | 4000Hz | 110 | −0.14 | 0.90 | −0.55 | 1.47 | −0.73 |
| 04 | RIGHT | 1000Hz | 82.5 | 0.22 | −1.64 | −1.24 | 1.30 | −0.71 |
| | | 2000Hz | 82.5 | 0.03 | 1.41 | −2.15 | 0.57 | −1.88 |
| | | 4000Hz | 72.5 | 0.05 | −1.27 | 0.49 | 2.31 | −1.43 |
| | LEFT | 1000Hz | 82.5 | −0.20 | 0.10 | −1.36 | 3.44 | 0.88 |
| | | 2000Hz | 82.5 | 0.59 | −2.08 | −0.14 | 0.78 | 0.71 |
| | | 4000Hz | 82.5 | 0.31 | −1.16 | −1.39 | 0.61 | 0.98 |
| 05 | RIGHT | 1000Hz | 90 | −1.50 | −0.55 | 0.49 | 0.14 | 2.07 |
| | | 2000Hz | 85 | 0.02 | 0.59 | 0.46 | 0.76 | 1.63 |
| | | 4000Hz | 80 | −1.26 | 0.23 | −0.21 | 0.41 | 0.63 |
| | LEFT | 1000Hz | 85 | −0.43 | 0.11 | −0.22 | 0.87 | 3.70 |
| | | 2000Hz | 87.5 | 0.30 | 0.48 | 0.44 | −0.14 | 0.42 |
| | | 4000Hz | 87.5 | 0.79 | 0.42 | −0.25 | 0.35 | 1.56 |
| ... | ... | ... | | ... | ... | ... | ... | ... |

NUMBER OF CHARACTERISTIC AMOUNTS COMBINED

NUMBER OF SOUND STIMULATIONS USED IN ESTIMATION

|  | 1000 Hz | 2000 Hz | 4000 Hz |
|---|---|---|---|
| RIGHT | 105 | 100 | 100 |
| LEFT | 100 | 95 | 100 |

UNCOMFORTABLE SOUND PRESSURE DETERMINATION SYSTEM, METHOD AND PROGRAM THEREOF, HEARING AID ADJUSTMENT SYSTEM, AND UNCOMFORTABLE SOUND PRESSURE DETERMINATION APPARATUS

This is a continuation of International Application No. PCT/JP2012/004244, with an international filing date of Jun. 29, 2012, which claims priority of Japanese Patent Application No. 2011-146093, filed on Jun. 30, 2011, the contents of which are hereby incorporated by reference.

BACKGROUND

1. Technical Field

The present disclosure relates to a technique of determining whether a pure tone has been heard in comfort. More specifically, the present disclosure relates to an uncomfortable sound pressure determination system for determining, when listening to a pure tone, a sound pressure that is felt so loud as to be uncomfortable; and the like.

2. Description of the Related Art

In recent years, people suffering from presbycusis are increasing in number due to the aging society. Due to the increased opportunities for listening to loud music for long hours as well as other influences, there is an increasing number of young people suffering from hypacusia associated with acoustic traumas. Moreover, due to the downsizing and improved performance of hearing aids, users have come to wear hearing aids with less of a psychological barrier. This has led to an increasing number of users wearing hearing aids.

A user suffering from hypacusia has difficulty in hearing sounds of a specific frequency(s). This specific frequency varies from user to user. A hearing aid amplifies the amplitude of a sound signal at this specific frequency, thus making it easier for the user to hear sounds.

A hearing aid is required to change the amount by which it amplifies sounds, in accordance with the level of deterioration in the hearing of the user. Therefore, before beginning use of a hearing aid, "fitting" is required for adjusting the amount of sound amplification in accordance with the hearing of each user.

The purpose of fitting is to keep the output sound pressure of a hearing aid at an MCL (most comfortable level). As used herein, the "output sound pressure" of a hearing aid refers to the fluctuations in air pressure that are perceivable to humans as a sound. The MCL defines a sound pressure which guarantees comfortable hearing by the user. The hearing aid needs to ensure that the output sound pressure satisfies MCL for each sound frequency.

Examples of inappropriate fitting may be: (1) an insufficient amount of amplification for sound pressure; or (2) an excessive amount of amplification for sound pressure. For example, if the amount of amplification for sound pressure is insufficient, the user cannot aurally distinguish audios. In this case, the aforementioned purpose of using a hearing aid is not met. If the amount of amplification for sound pressure is excessive, the user is capable of aural distinction of audios, but may find the audio to be loud, which prevents the user from using the hearing aid over a long time. Therefore, a fitting of a hearing aid needs to be done in such a manner that neither (1) nor (2) occurs. Especially, (2) possesses a possibility that the hearing aid may present an audio with an unduly high sound pressure to the user. This has created danger of hurting the user's ear with audios having high sound pressure.

Fitting generally comes into two steps. A first step of fitting is measuring an audiogram. An "audiogram" refers to a measurement of a threshold value (hearing threshold level: HTL) defining the smallest sound pressure of a pure tone that allows it to be heard by a user. An audiogram may be, for example, a diagram in which such a threshold value (decibel value) is plotted for different frequencies (e.g., 250 Hz, 500 Hz, 1000 Hz, 2000 Hz, 4000 Hz).

A second step of fitting is determining an amount of amplification for sound pressure. For example, by using a mathematical function (called a fitting theory) for estimating an amount of sound amplification, an amount of amplification is determined for each frequency and for each sound pressure of an input sound. There are a number of types of fitting theories, for example: the half-gain method, in which an insertion gain of each frequency is made half of the threshold value of that frequency; Berger's method, which slightly augments the amplify from 1000 Hz to 4000 Hz by taking into consideration the frequency band and level of conversational voices; the POGO method which, based on the half-gain method, reduces the gains at 250 Hz and 500 Hz (where there is not so much speech sound information but a lot of noise component is included) by 10 dB and 5 dB, respectively; and the NAL-R method, which performs amplification so that a frequency of long-term sound analysis of words will fall around a comfortable level.

Moreover, the "fitting theory" is also inclusive of a method of determining an amount of amplification for sound pressure by utilizing the information of a threshold value, a UCL (uncomfortable level) which is a high sound pressure level that is felt uncomfortable to the user, and the MCL. In that case, before determining an amount of amplification for sound pressure, the UCL and MCL are either measured or estimated. In order to avoid problem (2) above, it is necessary to measure the UCL, and set an amount of amplification in a range such that the UCL is not exceeded.

Similarly to audiogram measurement, a UCL is to be measured for each frequency. Conventionally, the UCL is measured based on subjective reporting. "Subjective reporting" involves, after a user hears a sound, the user making a subjective account as to how the sound was felt to him or her. For example, while using an audiometer, continuous sounds or discontinuous sounds are presented to the user by using an ascending method (i.e., the sound pressure level is gradually increased), and the user is asked to report whether the sound pressure is so loud that he or she cannot tolerate hearing it for a long time. Then, a sound pressure beyond which the user cannot retain tolerance over a long time, according to their own reporting, is defined as a UCL (Takashi KIMITSUKI et al., "Inner ear auditory testing in patients with normal hearing showing hyperacusis", 2009; hereinafter "Non-Patent Document 1").

An UCL measurement through subjective reporting is difficult because the UCL criterion will fluctuate under individual influences or the influences of linguistic expressions, and thus there is no established technique. Therefore, methods of taking an objectively measurement of UCL by using electroencephalogram are under development. For example, in a technique disclosed in Thornton, A. R. et al., "The objective estimation of loudness discomfort level using auditory brainstem evoked responses", 1987 (hereinafter "Non-Patent Document 2"), a UCL is estimated based on a relationship between the stimulation intensity and the latency of a V wave that is contained in a brainstem response called ABR (auditory brainstem response). As the sound pressure increases, the V wave latency decreases. The sound pressure of the sound which the user was hearing when the decrease in V wave latency became saturated is identified. A sound pressure which is obtained by adding a constant (e.g., 15 or 10) to this identified sound pressure is defined as the UCL.

SUMMARY

Conventional technique utilizes ABR, which is a weak signal component index, it is necessary that stimulations be repetitively presented, on the order of 1000 times. A test taking a long time is a burden on the user. Therefore, the prior art technique needs further reduction of the time of UCL estimation.

A non-limiting and illustrative embodiment of the present disclosure provides a technique of objectively measuring a UCL in less time.

In one general aspect, an uncomfortable sound pressure determination system according to an embodiment of the present disclosure includes: a biological signal measurement section configured to measure an electroencephalogram signal of a user; a sound data generation section configured to generate sound data concerning a plurality of sounds consecutively ascending or descending in sound pressure from first to $n^{th}$ sounds (n: an integer of two or more), the plurality of sounds being pure tones of a same frequency; an output section configured to present the plurality of sounds to the user based on the sound data; a characteristic amount extraction section configured to extract, based on an event-related potential of the electroencephalogram signal measured after lapse of a predetermined time from a point in time of presenting each of the plurality of sounds, a characteristic amount concerning temporal change in frequency of the event-related potential; and an uncomfortable sound pressure determination section configured to determine, by referring to a previously-provided relationship by which temporal changes in frequency of event-related potentials and uncomfortable sound pressures are associated, a sound pressure corresponding to the characteristic amount extracted by the characteristic amount extraction section to be an uncomfortable sound pressure at the frequency.

With an uncomfortable sound pressure determination system according to an embodiment of the present disclosure, pure tones of the same frequency are successively presented in monotonously ascending or monotonously descending sound pressures, totaling n times (n: an integer of two or more). Electroencephalographic characteristic amounts in response to the respective sound stimulations of first to $n^{th}$ sounds are extracted, and an UCL is estimated from a change pattern of the characteristic amounts. By relying on a change pattern of the characteristic amounts in response to the first to $n^{th}$ sounds having the same frequency and different sound pressures, it is possible to determine an uncomfortable sound pressure in less time and with a higher precision, away from the influence of individual differences. As a result, it becomes possible to set frequency gains so that the user will not be acoustically annoyed when wearing a hearing aid and will not be fatigued even after the hearing aid has been worn for a long time.

The general and specific aspects above may be implemented as a system, a method, or a computer program, or implemented by using a combination of a system, a method, and/or a computer program.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 4 includes: graphs (upper row) showing total arithmetic mean waveforms of event-related potentials at a central portion (Cz) obtained in response to first to fifth sounds, where the total arithmetic mean was taken irrespective of sound frequency; and graphs (lower row) showing P1-N1 amplitude and N1-P2 amplitude in the total arithmetic mean waveforms.

In FIG. 5, (a) and (b) are waveform diagrams showing waveforms obtained from arithmetic means, as classified by the magnitude of subjective UCL values.

FIG. 8 is a diagram showing an example of training data used in an uncomfortable sound pressure estimation.

DETAILED DESCRIPTION

Figures 1, 2:
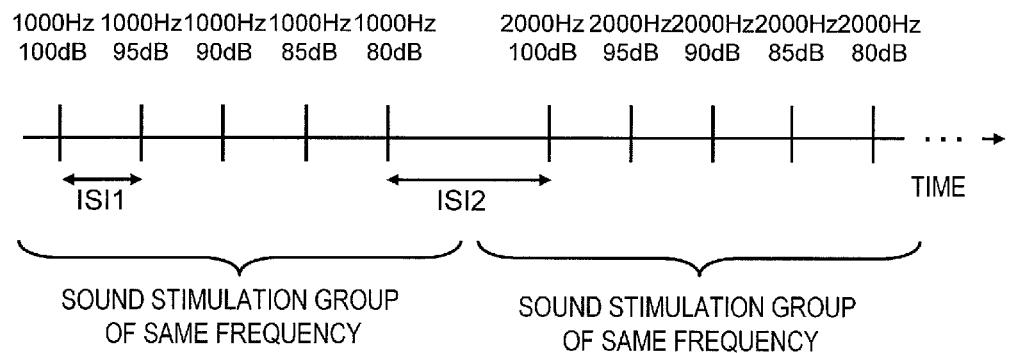
FIG. 1 is a diagram showing UCL measurement results of individuals measured through subjective reporting.
FIG. 2 is a schematic diagram showing sound stimulations in an electroencephalogram measurement experiment.

Conventional techniques of estimating a UCL using an electroencephalogram take time in the UCL estimation.

Exemplary embodiments disclosed herein and made by the inventors provide an solution(s) for the problem.

The following is an outline of an embodiment(s) of the present disclosure.

An uncomfortable sound pressure determination system according to an embodiment of the present disclosure comprises: a biological signal measurement section configured to measure an electroencephalogram signal of a user; a sound data generation section configured to generate sound data concerning a plurality of sounds consecutively ascending or descending in sound pressure from first to $n^{th}$ sounds (n: an integer of two or more), the plurality of sounds being pure tones of a same frequency; an output section configured to present the plurality of sounds to the user based on the sound data; a characteristic amount extraction section configured to extract, based on an event-related potential of the electroencephalogram signal measured after lapse of a predetermined time from a point in time of presenting each of the plurality of sounds, a characteristic amount concerning temporal change in frequency of the event-related potential; and an uncomfortable sound pressure determination section configured to determine, by referring to a previously-provided relationship by which temporal changes in frequency of event-related potentials and uncomfortable sound pressures are associated, a sound pressure corresponding to the characteristic amount extracted by the characteristic amount extraction section to be an uncomfortable sound pressure at the frequency.

For example, the sound data generation section includes: a sound stimulation group determination section configured to at least determine the frequency of the plurality of sounds; a detailing section configured to at least determine sound pressures of the first to $n^{th}$ sounds; and a sound stimulation generation section configured to generate sound data concerning a plurality of sounds having the frequency determined by the sound stimulation group determination section and having consecutively ascending or descending sound pressures from the first to $n^{th}$ sounds determined by the detailing section.

In one embodiment, the detailing section ensures that the sound pressures are ascending or descending by a predetermined difference from the first to $n^{th}$ sounds.

In one embodiment, the detailing section ensures that the sound pressures are ascending or descending by 5 dB from the first to $n^{th}$ sounds.

In one embodiment, the uncomfortable sound pressure determination section retains as training data a previously-provided relationship of one or more persons other than the user by which characteristic amounts concerning temporal changes in frequency of event-related potentials and sound pressures are associated, and performs linear discrimination by using the characteristic amount extracted by the characteristic amount extraction section against the training data.

In one embodiment, the sound stimulation group determination section determines whether the plurality of sounds are to be presented to a right or left ear; and the uncomfortable sound pressure determination section retains a plurality of pieces of said training data, each piece of training data concerning one of a right ear and a left ear and a frequency, and switches between the pieces of training data depending on whether the ear determined by the sound stimulation group determination section is right or left and depending on the frequency.

In one embodiment, the characteristic amount concerning temporal change in frequency of the event-related potential is a wavelet-coefficient related characteristic amount; and the characteristic amount extraction section extracts the wavelet-coefficient related characteristic amount based on an event-related potential of the electroencephalogram signal measured at a point in time not later than 300 ms from a point in time of presenting each of the plurality of sounds.

In one embodiment, the characteristic amount extraction section extracts as the characteristic amount a value obtained by averaging wavelet coefficients of the event-related potential over a predetermined frequency range and a predetermined time range.

In one embodiment, the predetermined frequency range is no less than 5 Hz and no more than 15 Hz.

In one embodiment, the predetermined time range is 50 ms.

In one embodiment, the uncomfortable sound pressure determination section determines the uncomfortable sound pressure by using the characteristic amounts in response to the first sound and the second sound.

In one embodiment, the uncomfortable sound pressure determination system further comprises a database in which uncomfortable sound pressures at the frequency are to be accumulated, the uncomfortable sound pressures being determined by the uncomfortable sound pressure determination section.

In one embodiment, the database accumulates an uncomfortable sound pressure for each of the right or left ear and for each frequency.

In one embodiment, the biological signal measurement section, a sound stimulation apparatus having the sound data generation section and the output section, and an uncomfortable sound pressure determination apparatus having the characteristic amount extraction section, the uncomfortable sound pressure determination section, and the database are interconnected.

A hearing aid adjustment system according to an embodiment of the present disclosure comprises a setting section configured to receive the uncomfortable sound pressure estimated by using the above uncomfortable sound pressure determination system, and setting the uncomfortable sound pressure to a hearing aid as a maximum output value.

An uncomfortable sound pressure determination apparatus according to an embodiment of the present disclosure comprises: a characteristic amount extraction section configured to extract a characteristic amount concerning temporal change in frequency of an event-related potential, when a plurality of sounds output from an output section are presented to a user, the plurality of sounds consecutively ascending or descending in sound pressure from first to $n^{th}$ sounds (n: an integer of two or more), based on the event-related potential of an electroencephalogram signal of the user measured by an electroencephalogram signal measurement section after lapse of a predetermined time from a point in time of presenting each of the plurality of sounds; and an uncomfortable sound pressure determination section configured to, by referring to a previously-provided relationship by which temporal changes in frequency of event-related potentials and uncomfortable sound pressures are associated, determine a sound pressure corresponding to the characteristic amount extracted by the characteristic amount extraction section to be an uncomfortable sound pressure at the frequency.

An uncomfortable sound pressure determination method according to an embodiment of the present disclosure comprises the steps of: measuring an electroencephalogram signal of a user; generating sound data concerning a plurality of sounds consecutively ascending or descending in sound pressure from first to $n^{th}$ sounds (n: an integer of two or more), the plurality of sounds being pure tones of a same frequency; presenting the plurality of sounds to the user based on the sound data; extracting, based on an event-related potential of the electroencephalogram signal measured after lapse of a predetermined time from a point in time of presenting each of the plurality of sounds, a characteristic amount concerning temporal change in frequency of the event-related potential; and determining, by referring to a previously-provided relationship by which temporal changes in frequency of event-related potentials and uncomfortable sound pressures are associated, a sound pressure corresponding to the characteristic amount extracted by the extracting step to be an uncomfortable sound pressure at the frequency.

An computer program according to an embodiment of the present disclosure is a computer program stored on a non-transitory computer-readable medium, and to be executed by a computer mounted in an uncomfortable sound pressure determination apparatus of an uncomfortable sound pressure determination system, wherein the computer program causes the computer to execute the steps of: acquiring an electroencephalogram signal of a user; generating sound data concerning a plurality of sounds consecutively ascending or descending in sound pressure from first to $n^{th}$ sounds (n: an integer of two or more), the plurality of sounds being pure tones of a same frequency; presenting the plurality of sounds to the user based on the sound data via an output section; extracting, based on an event-related potential of the electroencephalogram signal measured after lapse of a predetermined time from a point in time of presenting each of the plurality of sounds, a characteristic amount concerning temporal change in frequency of the event-related potential; and determining, by referring to a previously-provided relationship by which temporal changes in frequency of event-related potentials and uncomfortable sound pressures are associated, a sound pressure corresponding to the characteristic amount extracted by the extracting step to be an uncomfortable sound pressure at the frequency.

Hereinafter, with reference to the attached drawings, an uncomfortable sound pressure determination system according to an exemplary embodiment will be described.

An uncomfortable sound pressure determination system according to an exemplary embodiment is used to determine, by utilizing an electroencephalogram of a user when listening to a pure tone, whether the user has felt that the pure tone which he or she is hearing is loud. More specifically, the present system presents pure tones of the same frequency to the user totaling n times (n: an integer of two or more) in succession, with monotonously ascending or monotonously descending changes in sound pressure, extracts characteristic amounts of the user's electroencephalogram in response to the respective sound stimulations of first to $n^{th}$ sounds, and determine an uncomfortable sound pressure from a change pattern of the characteristic amounts.

First, the definitions of the terms used in the present specification will be described.

An "event-related potential (ERP)" is a fluctuation in the potential of an electroencephalogram (EEG) that occurs in response to a stimulation.

A "P1 component" is a positive potential which is induced at about 50 ms since the presentation of an auditory stimulation as a starting point.

An "N1 component" is a negative potential which is induced at about 100 ms since the presentation of an auditory stimulation as a starting point.

A "P2 component" is a positive potential which is induced at about 200 ms since the presentation of an auditory stimulation as a starting point.

An "uncomfortable sound pressure" is a sound pressure which is so loud as to make the user feel uncomfortable.

An "appropriate sound pressure" is a sound pressure within the range where the user does not feel uncomfortable.

"Presenting a sound" means outputting an auditory stimulation of a pure tone. For example, outputting a pure tone to only one ear from a pair of headphones falls within "presenting a sound".

A "pure tone" is a tone which repetitively undergoes periodic oscillation, such that it is expressed as a sine wave having only one frequency component.

In the exemplary embodiments, examples of using headphones to present a sound to a user will be illustrated. Although the headphones may be of any arbitrary type, they need to be able to precisely output a pure tone at a designated sound pressure for enabling correct determination of an uncomfortable sound pressure.

In the present specification, in order to define a component of an event-related potential, a point in time after the lapse of a predetermined time since a given point is expressed by referring to a "latency of about 100 ms", for example. This means possible inclusion of a range around the specific point of 100 ms. Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI—(or "Event-Related Potential (ERP) Manual—mainly concerning P300—"), edited by Kimitaka KAGA et al., Shinohara Shuppan Shinsha, 1995)". Therefore, the terms "about X ms" and "near X ms" mean that a breadth of 30 to 50 ms may exist before or after X ms (e.g., 100 ms±30 ms, 200 ms±50 ms).

1. Experimental Outline

The inventors have conducted the following two experiments in order to identify an electroencephalogram characteristic component that reflects an uncomfortable sound pressure concerning pure tones, for the purpose of realizing uncomfortable sound pressure determination for enabling objective determination of a UCL (uncomfortable level) in shorter time than conventionally.

One is a subjective report experiment where UCL is determined based on subjective reporting. The subjective report experiment was conducted twice, apart from an electroencephalogram measurement experiment below.

Another is an electroencephalogram measurement experiment where UCL is determined by using an electroencephalogram. In the electroencephalogram measurement experiment, pure tones of the same frequency were presented totaling five times in succession, with monotonous sound pressure changes of every 5 dBSPL, and event-related potentials in response to the respective sound stimulations of first to fifth sounds were measured.

The inventors conducted the experiment under the two conditions of: a crescendo condition where the sound pressures would monotonously ascend; and a decrescendo condition where sound pressures would monotonously descend, and, based on UCLs which were obtained from the subjective report experiment as reference data, looked for characteristic features of an event-related potential that is UCL-related.

Considering the results of the experiments, the inventors found that a UCL in a subjective report can be estimated on the basis of a change pattern of 'temporal change information concerning the frequency of an event-related potential' (hereinafter referred to as "temporal change information of event-related potential frequency") in response to each sound stimulation from among a plurality of sounds. A specific example of temporal change information of event-related potential frequency may be wavelet coefficients. The inventors have found that, by applying linear discrimination to the change pattern of wavelet coefficients which are calculated through a wavelet transform of event-related potentials, a UCL in a subjective report can be estimated. In the linear discrimination, change patterns of wavelet coefficients and UCL values from subjective reports of other people were used as training data. It has been found that this technique allows a UCL to be determined in a short time and with a high precision.

Hereinafter, these will be described in more detail. First, the electroencephalogram measurement experiment and the subjective report experiment under the two conditions, which were conducted by the inventors in order to realize uncomfortable sound pressure determination, will be described. Then, the construction and operation of embodiments of an uncomfortable sound pressure determination apparatus, and an uncomfortable sound pressure determination system including the uncomfortable sound pressure determination apparatus, will be described in outline.

2. Electroencephalogram Measurement Experiment and Subjective Report Experiment 2-1. Subjective Report Experiment The subjective report experiment was conducted twice, with a certain time interval therebetween. The experimental participants were 12 adults, who were no longer in school, having normal hearing (28 to 49 years old). Similarly to Non-Patent Document 1, continuous sounds were presented by ascending method using an audiometer, and an unbearably loud sound pressure was reported, this sound pressure being defined as the UCL. For each of three frequencies (1000 Hz, 2000 Hz, 4000 Hz) to be presented in the electroencephalogram measurement experiment, measurement was taken for both ears, one ear at a time. In order to prevent anticipation of the sound pressure, the sound pressure at the start of the experiment was randomly selected from among 60, 65, and 70 dBHL. The sound pressure of the continuous sound ascended by every 5 dB. An unbearably loud sound pressure was reported by raising a hand. Immediately after the participant raised a hand, the sound presentation was stopped, and the sound pressure was recorded.

Hereinafter, results of the subjective report experiment will be described.

The results of the subjective report experiment greatly differed from individual to individual, although all participants were people with normal hearing, with the largest difference of 40 dB at the same frequency. This indicates that the definition of "unbearably loud" may greatly from individual to individual. Thus, it can be said that UCL determination through subjective reporting is difficult.

FIG. 1 shows UCL measurement results of individuals which were measured through subjective reporting in the subjective report experiment. FIG. 1 indicates average values of two measurement results each. The sound pressure is in units of dBHL. As can be seen from the standard deviation for the right or left ear and for each different frequency shown in FIG. 1, there are large fluctuations among individuals. Moreover, a variance analysis which was performed for repeated measurements with respect to the factors of right or left and frequency indicated that there was no significant interaction ($p=0.169$). Moreover, the there was no significant principal effect in terms of right or left, or frequency ($p=0.108$, $p=0.124$).

Therefore, it can be said that the UCL measurement results through subjective reporting exhibited no right/left dependence and no frequency dependence. Note that, with respect to each participant and each frequency, the two measurement results in the subjective report experiment fluctuated by 5 dB or more in about 60% of all results. This means that the uncomfortable sound pressure determination through subjective reporting involves some ambiguity.

2-2. Electroencephalogram Measurement Experiment

In the electroencephalogram experiment, for each of three frequencies (1000 Hz, 2000 Hz, 4000 Hz), sound stimulations were presented totaling five times in succession with monotonously ascending or descending sound pressures, thus resulting in five sound pressures that are presumably near the UCL sound pressure (80 dBSPL, 85 dBSPL, 90 dBSPL, 95 dBSPL, 100 dBSPL), and characteristic amount variation among event-related potentials in response to different sound stimulations was examined. Hereinafter, with reference to FIGS. 2 to 11, the experimental setting and experimental results of the electroencephalogram measurement experiment will be described.

The experimental participants were the same 12 adults in the subjective report experiment, who were no longer in school and who had normal hearing (28 to 49 years old).

The sound stimulations were tone burst sounds with a duration of 50 ms. Each sound stimulation had a rise and fall of 3 ms each. For each of the three frequencies (1000 Hz, 2000 Hz, 4000 Hz), characteristic amount variation in the event-related potential against changing sound pressure was examined, by using sound stimulations of the five sound pressures (80 dBSPL, 85 dBSPL, 90 dBSPL, 95 dBSPL, 100 dBSPL). A group of sound stimulations pertaining to the same frequency will be referred to as a sound stimulation group.

By using a crescendo condition where the sounds ascended in sound pressure and a decrescendo condition where the sounds descended in sound pressure, each sound stimulation group was presented to the user. Under the crescendo condition, sound stimulations of the same frequency were presented with stepwise increments in the sound pressure of the sound stimulations by every 5 dB, from 80 dBSPL to 100 dBSPL. Under the decrescendo condition, sound stimulations of the same frequency were presented with stepwise decrements in the sound pressure of the sound stimulations by every 5 dB, from 100 dBSPL to 80 dBSPL.

The sound stimulations contained in the sound stimulation group were presented to the same ear at predetermined intervals. The crescendo condition and the decrescendo condition were pursued separately. Care was taken so that the experimental order of the crescendo condition and the decrescendo condition was counterbalanced among the participants. Each sound stimulation was presented to one ear through headphones.

FIG. 2 schematically shows sound stimulations in the electroencephalogram measurement experiment.

The participants were instructed that there was no need to pay attention to the sound stimulations. In either condition, the interval between successively-presented sound stimulations within a sound stimulation group of the same frequency (ISI1 in FIG. 2) was fixed at 300 ms. Moreover, the interval between sound stimulation groups (ISI2 in FIG. 2) was randomly decided within a range of 450±100 ms. The sound stimulation group for the right or left ear and for each different frequency was each repeated 30 times (totaling in 180 sound stimulation groups, and 900 (180×5) sound stimulations).

In order to reduce taming (habituation) of the auditory evoked potential due to successive presentation of the same sound stimulation group, the frequency and the ear for which to present the sound stimulation group were determined under the following constraints: the frequency is selected to be different from that of an immediately previous sound stimulation group; the ear to which the sound stimulation group is presented is randomly selected between right and left; however, in order to ensure randomness of stimulations between the right and left ears, not more than four sound stimulation groups are successively presented to either the right or left ear.

Figure 3A:
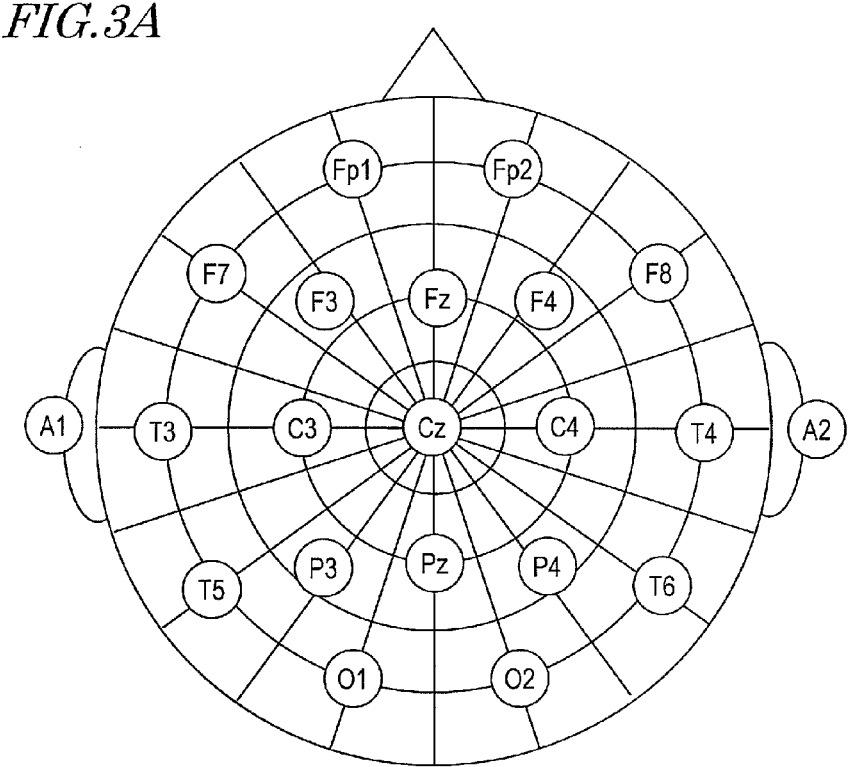
FIG. 3A is a diagram showing electrode positions according to the International 10-20 system (10-20 System)
Figure 3B:
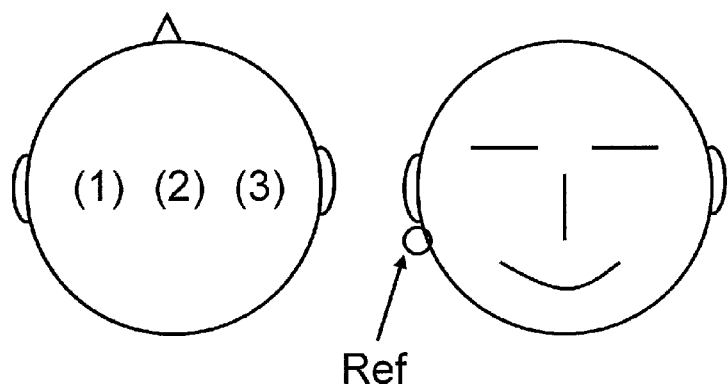
FIG. 3B is a diagram showing electrode positioning in the present experiment.

The electroencephalogram was recorded from C3, Cz, and C4 (the International 10-20 system) on the scalp, on the basis of the right mastoid. A "mastoid" is a protrusion of the cranium below the hind root of an ear. FIG. 3A shows electrode positions according to the International 10-20 system (10-20 System). FIG. 3B shows electrode positioning as to how electrodes were worn in the present experiment. In FIG. 3B, (1), (2), and (3) represent the electrode positions C3, Cz, and C4, respectively.

The sampling frequency was 1000 Hz; the time constant was 0.3 seconds; and an analog low-pass filter was applied at 30 Hz. The entire time slot of electroencephalogram data measured was subjected to a 5-20 Hz digital band-pass filter off-line. Thereafter, as an event-related potential in response to a sound stimulation for the right or left ear, for each different frequency, and for each different sound pressure, a waveform from −100 ms to 400 ms was cut out based on the respective sound stimulation as a starting point. As used herein, "−100 ms" means a point in time which is 100 milliseconds before the point in time at which a sound stimulation is presented.

Moreover, for each sound stimulation, temporal change information of event-related potential frequency was derived with respect to an electroencephalogram waveform in a range from 0 ms to 300 ms of the event-related potential. As an example, a continuous wavelet transform was performed to calculate a wavelet coefficient for each time and each frequency. As a mother wavelet, the Mexican hat function ($\phi(t) = (1-t^2)\exp(-t^2/2)$) was used.

The waveforms and wavelet coefficients of event-related potential were arithmetic-meaned, for each condition, each individual person, each of the right or left ear, each frequency, and each sound stimulation group of first to fifth sounds. These will be referred to as, respectively, the arithmetic mean waveform and the arithmetic mean wavelet coefficient. Those trials which exhibited an amplitude in absolute value of 50 μV or more at any electrode were excluded from the total arithmetic mean and arithmetic mean, because they presumably are under the influence of noises, e.g., eye movements and blinks. Then, as characteristic amounts of the event-related potential potentially serving as indices of uncomfortable sound pressure, average values of the arithmetic mean wavelet coefficients over a frequency range from 5 Hz to 15 Hz were calculated in every time range of 50 ms (hereinafter referred to as wavelet characteristic amounts).

Hereinafter, results of the electroencephalogram measurement experiment will be described.

For general explanation of the electroencephalogram measurement experiment results, FIG. 4 shows (upper row) total arithmetic mean waveforms of event-related potentials at a central portion (Cz) obtained in response to the first to fifth sounds, where the total arithmetic mean was taken irrespective of sound frequency, and shows (lower row) P1-N1 amplitude and N1-P2 amplitude in the total arithmetic mean waveforms.

Each total arithmetic mean waveform is a waveform obtained by taking an arithmetic mean of arithmetic mean waveforms (calculated by the aforementioned method) across individuals, irrespective of sound frequency. The upper left graph shows total arithmetic mean waveforms under the crescendo condition, whereas the upper right graph shows total arithmetic mean waveforms under the decrescendo condition. The horizontal axis represents time in units of ms, and the vertical axis represents potential in units of μV. On the horizontal axis, 0 ms marks a point in time at which the sound stimulation is presented. As indicated on the vertical axis of FIG. 4, the lower direction in the graphs corresponds to plus (positive), and the upper direction corresponds to minus (negative).

As exemplification of the results, waveforms in response to the first sound, the third sound, and the fifth sound are shown with a bold solid line, a broken line, and a thin solid line, respectively. The second sound and fourth sound are omitted in order to avoid complexity of illustration.

The sound pressure of the first sound was 80 dBSPL under the crescendo condition, and 100 dBSPL under the decrescendo condition. The sound pressure of the third sound was 90 dBSPL in either condition. The sound pressure of the fifth sound was 100 dBSPL under the crescendo condition, and 80 dBSPL under the decrescendo condition. It is indicated that, for any sound stimulation, an N1 component (negative peak) is induced at 100 ms since the presentation of the sound stimulation.

The P1-N1 amplitude shown in the lower row of FIG. 4 was calculated by subtracting a zone average potential at 10 ms before or after a negative peak of the N1 component from a zone average potential at 10 ms before or after a positive peak of the P1 component induced at about 50 ms since the presentation of the sound stimulation. The N1-P2 amplitude was calculated by subtracting a zone average potential at 10 ms before or after a negative peak of the N1 component from a zone average potential at 25 ms before or after a positive peak of the P2 component induced at about 200 ms after since the presentation of the stimulation. The horizontal axis represents sound pressure in units of dBSPL, and the vertical axis represents amplitude in units of μV. White circle indicate P1-N1 amplitude, and black circles indicate N1-P2 amplitudes. The change characteristics of the P1-N1 amplitude and the N1-P2 amplitude both greatly differed depending on the condition. As shown in the lower left graph of FIG. 4, the amplitude under the crescendo condition is largest for the sound stimulation of 80 dBSPL, i.e., the first sound, and from there decreases toward the second sound and the third sound, but thereafter increases toward the fourth sound and the fifth sound. As shown in the lower right graph of FIG. 4, the amplitude under the decrescendo condition is largest for the sound stimulation of 100 dBSPL, i.e., the first sound, and from there steeply decreases toward the second sound and the third sound, and thereafter gently decreases toward the fourth sound and the fifth sound. What may account for the different change characteristics of amplitude depending on the condition is that: the pattern of changes in sound pressure differed between the monotonously ascending condition and the monotonously descending condition; the frequency was changed between sound stimulation groups; and the stimulations were presented randomly to the right or left ear.

In FIG. 5, (a) and (b) show waveforms obtained from arithmetic means, as classified by the magnitude of subjective UCL values. Graphs (a) and (b) of FIG. 5 show waveforms of continuous electroencephalogram data measured at the central portion (Cz) from 100 ms before presentation of the first sound to 400 ms after presentation of the fifth sound, where separate arithmetic means were taken depending on whether the subjective UCL value was greater than 95 dBHL or was equal to or less than 95 dBHL, irrespective of sound frequency and irrespective of the right or left ear. The bold line indicates an arithmetic mean waveform of the case where the subjective UCL value is greater than 95 dBHL, whereas the thin line indicates that of the case where the subjective UCL value is equal to or less than 95 dBHL. A baseline correction has been applied on the basis of 100 ms before presentation of the first sound. FIG. 5(a) shows arithmetic mean waveforms under the crescendo condition, whereas FIG. 5(b) shows arithmetic mean waveforms under the decrescendo condition. The horizontal axis represents time in units of ms, and the vertical axis represents potential in units of μV. On the horizontal axis, 0 ms marks a point in time of presenting the first sound. In (a) and (b) of FIG. 5, timings with which the sound stimulations of first to fifth sounds were presented were indicated by a dotted line. FIG. 5(a) (crescendo condition) indicates that the N1-P2 amplitude in response to the second sound is smaller when the subjective UCL value is small (thin line) than when it is large (bold line), and FIG. 5(b) (decrescendo condition) indicates that the N1-P2 amplitudes in response to the second and third sounds are smaller when the subjective UCL value is small (thin line) than when it is large (bold line).

Figure 6A:
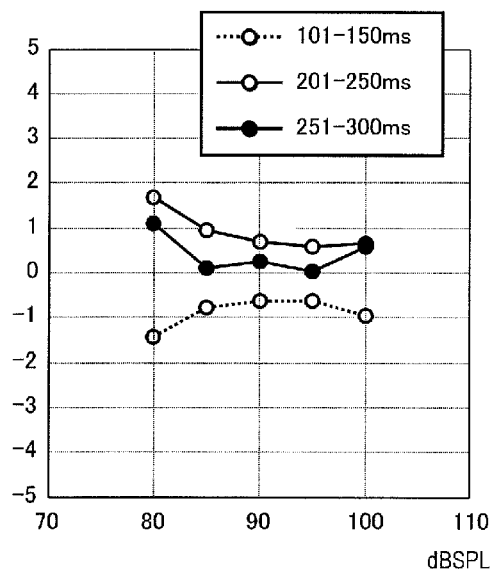
FIGS. 6A and 6B are graphs showing wavelet characteristic amounts at a central portion (Cz) obtained in response to first to fifth sounds, where the values are obtained through a total arithmetic mean irrespective of frequency.
Figure 6B:
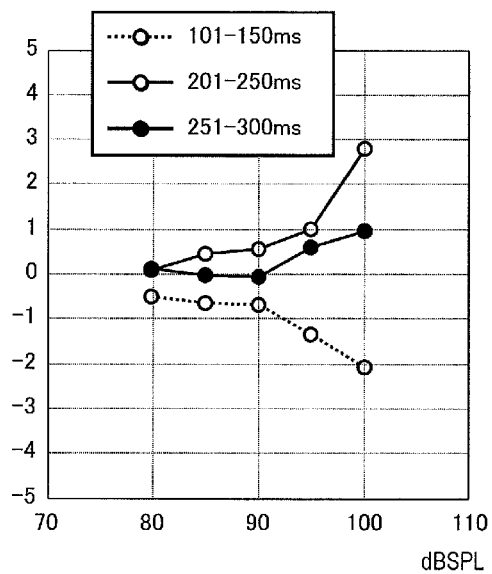

FIGS. 6A and 6B show wavelet characteristic amounts at the central portion (Cz) obtained in response to the first to fifth sounds, where the values are obtained through a total arithmetic mean irrespective of frequency. FIG. 6A shows total arithmetic mean values under the crescendo condition, whereas FIG. 6B shows total arithmetic mean values under the decrescendo condition.

As exemplification of the results, total arithmetic mean values of wavelet characteristic amounts at 101-150 ms, 201-250 ms, and 251-300 ms since the presentation of the sound stimulation, in which wavelet characteristic amounts exhibited large changes between sound pressure levels of the sound stimulations, are indicated by white circles connected by broken lines, white circles connected by solid lines, and black circles connected by solid lines, respectively.

Similarly to the P1-N1 amplitude and the N1-P2 amplitude, the wavelet characteristic amounts shown in FIGS. 6A and 6B also exhibited differences between the two conditions. In addition, the change characteristics of the wavelet characteristic amounts differed depending on the time slot in which the wavelet characteristic amount was calculated. For example, under the decrescendo condition, the wavelet characteristic amount at 101-150 ms showed no change from the sound stimulation of 80 dBHL to the sound stimulation of 90 dBHL, but monotonously decreased beyond 90 dBHL; on the other hand, the wavelet characteristic amount at 201-250 ms gently increased from 80 dBHL to 95 dBHL, but steeply increased at 100 dBHL. Thus, the wavelet characteristic amount exhibits different characteristics depending on the time slot, indicative of a possibility that the accuracy of estimation of an uncomfortable sound pressure may be improved depending on the combination of characteristic amounts.

2-3. Uncomfortable Sound Pressure Estimation

First, in order to confirm that an index of uncomfortable sound pressure estimation exists in the characteristic amount variation in the event-related potential against changing sound pressure, the relationship between the subjective UCL value and the wavelet characteristic amount was exampled. Then, in order to ascertain the precision of uncomfortable sound pressure estimation using such characteristic amount variation, a discriminant analysis was conducted. These will be specifically described below.

For enabling estimation of an uncomfortable sound pressure based on an event-related potential, a characteristic amount that reflects a subjective UCL value for each participant needs to exist. However, as discussed above, the subjective UCL value can only be an index that is prone to fluctuations among participants, because of different personalities existing with respect to overbearing sounds. This makes it difficult to apply data of each individual person to the identification of presence or absence of a characteristic amount that reflects a subjective UCL value. Therefore, in order to reduce such fluctuations, differences in the characteristic amounts were examined while making a distinction between large subjective UCL values and small subjective UCL values. Specifically, an arithmetic mean of wavelet characteristic amounts was taken with respect to the cases where the subjective UCL value for each participant and for each frequency was larger than 95 dBHL, or the cases where it was equal to or less than 95 dBHL, and these results were compared. Note that 95 dBHL is a value near the center of the subjective UCL values of all participants obtained from the subjective report experiment, and there were substantially the same number of cases where the subjective UCL value was larger than 95 dBHL as the cases where it was equal to or less than 95 dBHL.

Figure 7A:
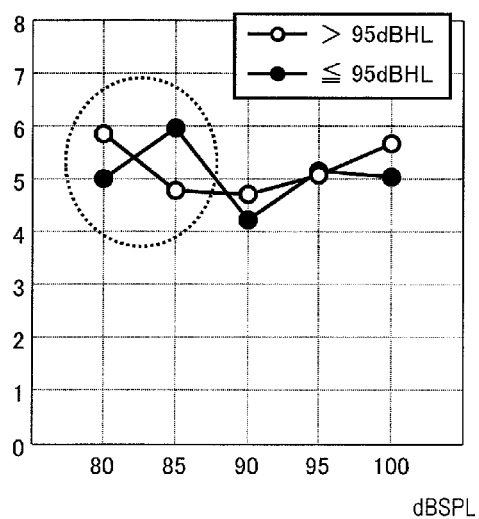
FIGS. 7A and 7B are graphs, under respectively different conditions, showing wavelet characteristic amounts for different subjective UCL value ranges.
Figure 7B:
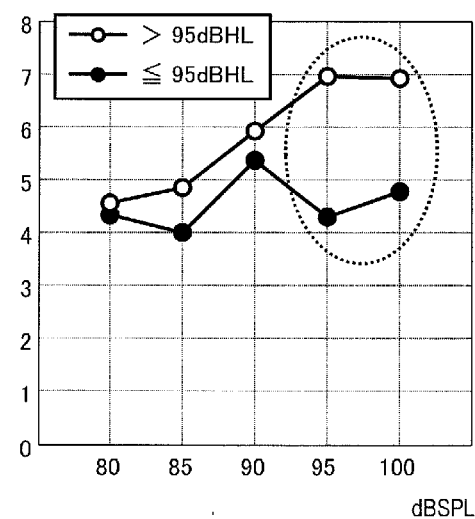

FIGS. 7A and 7B under respectively different conditions, showing wavelet characteristic amounts for different subjective UCL value ranges. As exemplary results, FIGS. 7A and 7B show wavelet characteristic amounts in the time slot from 251 ms to 300 ms. Specifically, FIG. 7A shows results under the crescendo condition, whereas FIG. 7B shows results under the decrescendo condition. Under the crescendo condition as shown in FIG. 7A, the difference associated with the different subjective UCL values was greater in the wavelet characteristic amounts in response to the sound stimulations of the first sound of 80 dBSPL and the second sound of 85 dBSPL than in the wavelet characteristic amounts in response to other sound stimulations (i.e., the third to fifth sounds). On the other hand, under the decrescendo condition as shown in FIG. 7B, the wavelet characteristic amounts in response to the sound stimulations of the first and second sounds of 100 dBSPL and 95 dBSPL clearly differed depending on the subjective UCL value. Specifically, the wavelet characteristic amounts in response to the sound stimulations of 100 dBSPL and 95 dBSPL were greater in the case where the subjective UCL value was larger than 95 dBHL than in the subjective UCL value is equal to or less than 95 dBHL.

It was made clear by these results that characteristic amount variation in the event-related potential against changing sound pressure will differ at least depending on the difference between subjective UCL values. This indicates a possibility that an index of uncomfortable sound pressure estimation may reside in characteristic amount variation.

Next, in order to ascertain the precision of an uncomfortable sound pressure estimation using characteristic amount variation in the event-related potential, a discriminant analysis was conducted. Linear discrimination was used as the technique of discriminant analysis, which was conducted by allowing the subjective UCL value for each of the right or left ear and for each frequency obtained through the aforementioned subjective report experiment to be "trained" (associated) with a wavelet characteristic amount of an event-related potential for each sound pressure. In order to find characteristic amounts that are suitable for uncomfortable sound pressure estimation, the error of each characteristic amount (alone or in combination with any other(s)) with respect to the subjective UCL value was ascertained, and a comparison was made between errors resulting from different numbers of characteristic amounts used in combination. As described above, depending on its time slot, a wavelet characteristic amount has different change characteristics. Therefore, since the UCL criterion will vary depending on the combination, there is a possibility of attaining UCL estimation with less error. In other words, since wavelet characteristic amounts are differentiated based on time slots, UCL estimation may be attained with less error by adapting the combination based on which time slot to obtain data from.

Hereinafter, the data to be used in linear discrimination, and the linear discrimination conducted will be described. FIG. 8 shows an example of training data used in an uncomfortable sound pressure estimation. Each subjective UCL value shown in FIG. 8 was measured through the subjective report experiment for each participant, each of the right or left ear, and each frequency. In FIG. 8, the columns corresponding to the first to fifth sounds show characteristic amounts of the event-related potentials in response to the first to fifth sounds of a sound stimulation group. As exemplification of characteristic amounts, FIG. 8 shows wavelet characteristic amounts at 251-300 ms under the decrescendo condition. These characteristic amounts for each sound stimulation group were associated with the respective subjective UCL value, for use as training data in a linear discrimination to be conducted.

The linear discrimination was conducted by using target data and training data. The target data for linear discrimination was the characteristic amounts of the event-related potentials for the sound stimulation group, taken for a given participant. The training data was generated from the characteristic amounts of event-related potentials of people other than the participant. Specifically, the training data was generated from the characteristic amounts of the event-related potentials of other people for each condition, each of the right or left ear, and each frequency. For example, if the target data for linear discrimination was that of participant 01 for the right ear and 1000 Hz, the training data was generated from the characteristic amounts of the data of the event-related potential for the right ear and 1000 Hz from a participant other than participant 0. As the characteristic amounts, the aforementioned wavelet characteristic amounts (time range 50 ms) were used.

In order to explore the possibility of uncomfortableness threshold estimation, in the case where a plurality of characteristic amounts were to be employed in combination, characteristic amounts were added in extra columns, in either the target data for linear discrimination or the training data. For example, if wavelet characteristic amounts from 151 ms to 200 ms and wavelet characteristic amounts from 251 ms to 300 ms were to be employed in combination, in addition to the first to fifth columns being allocated to the characteristic amounts in response to the first to fifth sounds regarding the former, sixth to tenth columns were allocated to the characteristic amounts in response to the first to fifth sounds regarding the latter. These can be treated as vectorized data. An "estimation error" was defined as the absolute value of a difference between a subjective UCL value and a result of uncomfortable sound pressure estimation. Accuracy of estimation was measured on the basis of an average estimation error, which was obtained by averaging the estimation errors of all participants with respect to right and left and all frequencies.

Figure 9A:
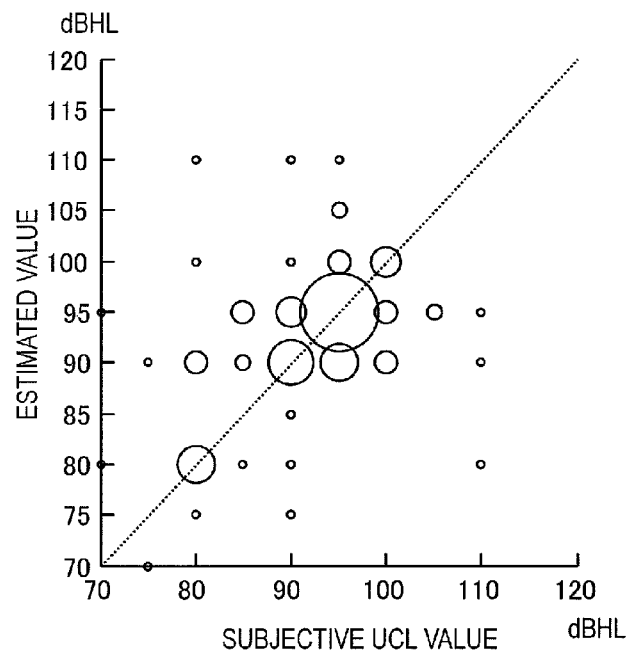
FIGS. 9A and 9B are graphs showing, as exemplification of linear discrimination results, distributions under different conditions of results of uncomfortable sound pressure estimation based on subjective UCL values and linear discrimination, in the case where two characteristic amounts are used in combination.
Figure 9B:
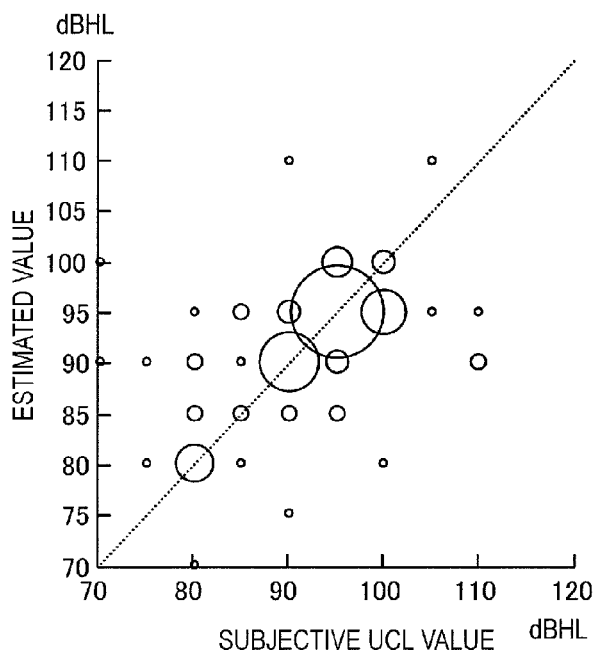

FIGS. 9A and 9B show, as exemplification of linear discrimination results, distributions under different conditions of results of uncomfortable sound pressure estimation based on subjective UCL values and linear discrimination, in the case where two characteristic amounts are used in combination. FIG. 9A shows results under the crescendo condition, and FIG. 9B shows results under the decrescendo condition. The analysis was conducted for each condition, each of the right or left ear, and each frequency; however, FIGS. 9A and 9B each show the results altogether, irrespective of the right or left ear or frequency. As indicated by the scales in FIGS. 9A and 9B, the horizontal axis represents subjective UCL values in units of dBHL, and the vertical axis represents uncomfortable sound pressure estimation values in units of dBHL. Results of uncomfortable sound pressure estimation with respect to subjective UCL values are indicated by ○ symbols as lattice points. The size of any ○ symbol reflects the frequency distribution of the particular estimation result. The average estimation error was 6.5 dB under the crescendo condition, and 5.4 dB under the decrescendo condition. From the results under both conditions, it can be seen that uncomfortable sound pressures which are correlated with the subjective UCL values have successfully been estimated, although there are some fluctuations. In the case where two characteristic amounts were used in combination, the coefficient of correlation between the subjective UCL values and the results of uncomfortable sound pressure estimation was 0.35 under the crescendo condition, and 0.45 under the decrescendo condition.

Figure 10:
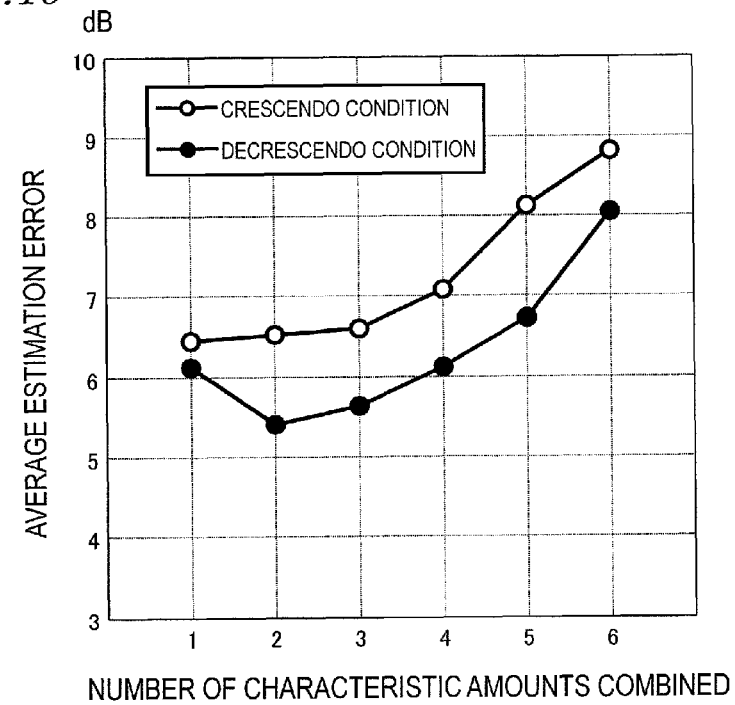
FIG. 10 is a graph showing transitions in the average estimation error with different numbers of characteristic amounts combined.

FIG. 10 shows transitions in the average estimation error with different numbers of characteristic amounts combined. In FIG. 10, the horizontal axis represents the number of characteristic amounts combined, and the vertical axis represents the average estimation error. Results under the crescendo condition are indicated by white circles, whereas results under the decrescendo condition are indicated by black circles. It can be seen that, irrespective of the number of characteristic amounts combined, the average estimation error is smaller under the decrescendo condition than under the crescendo condition. Also, under the decrescendo condition, there are cases where using a combination of characteristic amounts led to a smaller average estimation error than when using a single characteristic amount (number of characteristic amounts combined: 1). Specifically, the average estimation error was small in the case where two to four characteristic amounts were used in combination. For example, in the case where two characteristic amounts were used in combination, the smallest average estimation error was attained by a combination of the wavelet characteristic amount from 201 ms to 250 ms and the wavelet characteristic amount from 251 ms to 300 ms. However, when five or more characteristic amounts were used in combination, the average estimation error became larger than when a single characteristic amount was used. This implies that the estimation error can be minimized by adopting an optimum number of characteristic amounts in combination. In this instance, since six wavelet characteristic amounts were used for each condition, each of the right or left ear, each frequency, and each sound pressure, it might be possible that characteristic amounts serving as noises for uncomfortable sound pressure estimation were abundant when five or more characteristic amounts were used in combination. It can be said that the optimum number of characteristic amounts to be combined fluctuates depending on the selection of characteristic amounts. On the other hand, in this instance, the results under the crescendo condition indicated that the average estimation error is smallest when the number of characteristic amounts combined is 1. However, depending on the selection of characteristic amount (e.g., using thirty wavelet characteristic amounts that are 10 ms apart), it is presumable the average estimation error would be smallest under an optimum combination number of two or more, similarly to the decrescendo condition.

Figure 11:
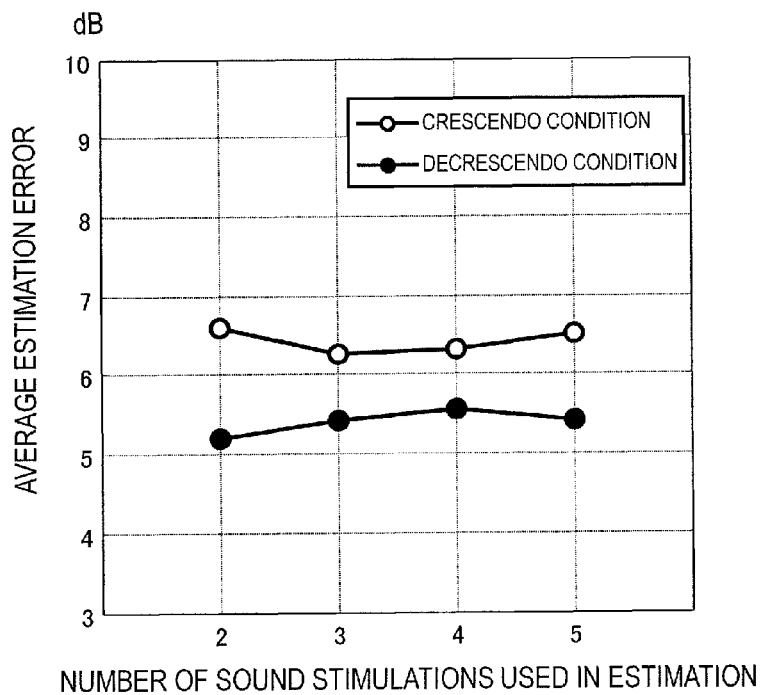
FIG. 11 is a graph showing average estimation errors in the case where sound stimulations up to an $n^{th}$ sound are used in uncomfortable sound pressure estimation under different conditions.

The above-described results are directed to the case where all of the first to fifth sounds of the sound stimulation group (five sound pressures, 80 to 100 dBSPL) that were employed in the electroencephalogram measurement experiment are utilized in discriminant analysis. Next, in order to ascertain up to which sound an analysis needs to be carried in making an uncomfortable sound pressure estimation, discriminant analyses were conducted by exclusively using wavelet characteristic amount data concerning the first to $n^{th}$ sounds under each condition. For example, when using wavelet characteristic amounts in response to the first to third sounds, characteristic amounts in response to the fourth and fifth sounds were excluded. FIG. 11 shows average estimation errors in the case where sound stimulations up to an $n^{th}$ sound are used in uncomfortable sound pressure estimation under different conditions. Note that the results shown in FIG. 11 are those in the case where two characteristic amounts were used in combination. Results under the crescendo condition are indicated by white circles, whereas results under the decrescendo condition are indicated by black circles. Under the crescendo condition, the average estimation error was smallest when characteristic amounts in response to the first to third sounds were used. Under the decrescendo condition, the average estimation error was smallest when characteristic amounts in response to the first to second sounds were used. Thus, it can be said that the number of sound stimulations that is suitable for uncomfortable sound pressure estimation differs depending on the condition: from the first to third sounds under the crescendo condition, and from the first to second sounds under the decrescendo condition.

These results are also consistent with the results indicated in FIG. 7B that, under the decrescendo condition, the difference between subjective UCL values was clearly reflected in the wavelet characteristic amounts in response to the first sound (100 dBSPL) and the second sound (95 dBSPL).

Note that, instead of using wavelet characteristic amounts, P1-N1 amplitude and N1-P2 amplitude information may be utilized in making a discriminant analysis, for example. As shown in (a) and (b) of FIG. 5, the N1-P2 amplitudes in response to the second and third sounds are smaller when the subjective UCL value is equal to or less than 95 dBHL than when the subjective UCL value is greater than 95 dBHL. Therefore, it is considered that uncomfortable sound pressure estimation is possible by comparing the N1-P2 amplitudes in response to the second sound against a predetermined threshold value, for example.

Note that training data may be generated irrespective of the right or left ear and irrespective of sound frequency.

Thus, it has been made clear through the subjective report experiment and electroencephalogram measurement experiment carried out by the inventors that, when pure tones of the same frequency are presented totaling five times in succession at monotonously ascending or monotonously descending sound pressures, it is possible to estimate an uncomfortable sound pressure by using temporal change information (which in one example may be characteristic amounts related to wavelet coefficients) concerning the frequency of electroencephalographic event-related potentials in response to the respective sound stimulations of first to fifth sounds.

Hereinafter, an uncomfortable sound pressure determination system according to an exemplary embodiment will be described. The uncomfortable sound pressure determination system presents pure tones of the same frequency totaling n times in succession at monotonously ascending or monotonously descending sound pressures, and achieves an uncomfortable sound pressure determination based on a change pattern in electroencephalographic characteristic amounts in response to the respective sound stimulations of first to $n^{th}$ sounds. This is unprecedentedly realized based on the aforementioned findings of the inventors.

Embodiment 1

Hereinafter, an uncomfortable sound pressure determination system will be described in outline first. Thereafter, the construction and operation of an uncomfortable sound pressure determination system including the uncomfortable sound pressure determination apparatus will be described.

An uncomfortable sound pressure determination system according to the present embodiment presents pure tones of the same frequency totaling n times (where n is an integer of two or more) at monotonously ascending or monotonously descending sound pressures, extracts electroencephalographic characteristic amounts in response to the respective sound stimulations of first to $n^{th}$ sounds, and determines an uncomfortable sound pressure from a change pattern of the characteristic amounts.

In the present embodiment, the amplitude level and polarity of a characteristic component of an event-related potential may vary depending on the positions at which the electrodes for electroencephalogram measurement (a reference electrode, a probe electrode, etc.) are worn.

However, based on the following description, those skilled in the art should be able to make appropriate modifications depending on the specific reference electrode and probe electrode, and extract a characteristic feature of an event-related potential and determine an uncomfortable sound pressure. Any such variant is encompassed within the present disclosure.

Figure 12:
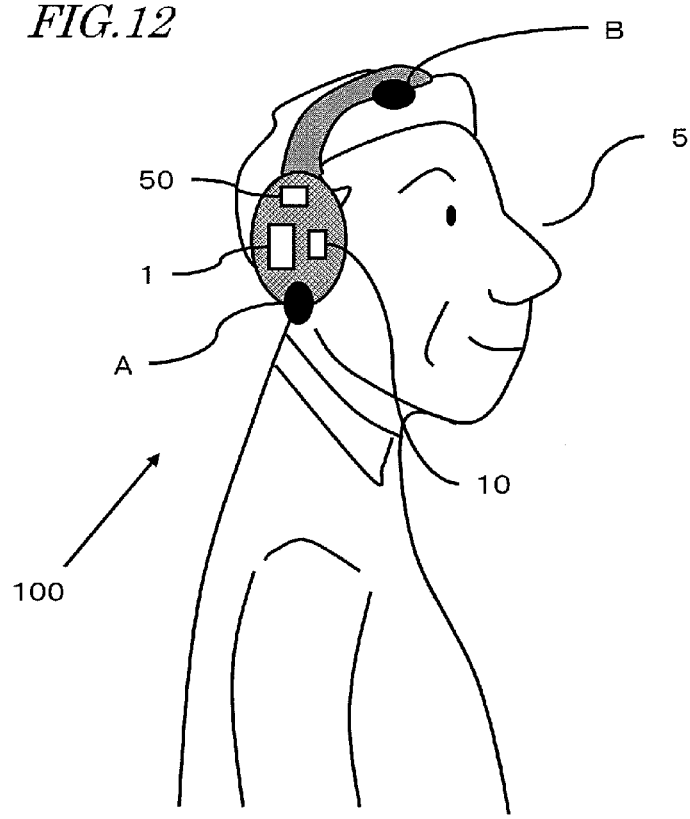
FIG. 12 is a diagram showing a construction and an environment of use for an uncomfortable sound pressure determination system 100 according to an exemplary embodiment.

FIG. 12 shows a construction and an environment of use for the uncomfortable sound pressure determination system 100 of the present embodiment. The uncomfortable sound pressure determination system 100 corresponds to a system construction of Embodiment 1 described below.

The uncomfortable sound pressure determination system 100 includes an uncomfortable sound pressure determination apparatus 1, a sound stimulation output section 10, and a biological signal measurement section 50.

The sound stimulation output section 10 outputs sound stimulations to the user 5.

The biological signal measurement section 50 is connected to at least two electrodes A and B. For example, electrode A is attached at a mastoid of the user 5, whereas electrode B is attached at the central portion (so-called Cz) of the scalp of the user 5. The biological signal measurement section 50 measures an electroencephalogram of the user 5 corresponding to a potential difference between electrode A and electrode B.

The uncomfortable sound pressure determination system 100 determines a sound stimulation group (first to $n^{th}$ sounds) of a certain frequency to be presented at monotonously ascending or monotonously descending sound pressures. Then, it presents the determined sound stimulation group to either the right or left ear in random order, and, as temporal change information concerning frequency, extracts wavelet coefficients of the electroencephalogram (event-related potentials) of the user 5 measured based on the points in time of presenting the first to $n^{th}$ sounds as starting points. Furthermore, from a change pattern of the characteristic amounts in response to the first to $n^{th}$ sounds, an uncomfortable sound pressure for that user is estimated.

The details of the respective component elements will be described later.

In the uncomfortable sound pressure determination apparatus 1 shown in FIG. 12, the biological signal measurement section 50 and the sound stimulation output section 10 are accommodated within the same housing. Alternatively, the biological signal measurement section 50 and the sound stimulation output section 10 of the uncomfortable sound pressure determination apparatus 1 may be in separate housings. In that case, an electroencephalogram signal measured by the biological signal measurement section 50 is sent to the uncomfortable sound pressure determination apparatus 1 which is connected in a wireless or wired manner.

The uncomfortable sound pressure determination apparatus 1 determines the right or left ear, frequency, sound pressure, and timing for sound stimulations for uncomfortable sound pressure determination. The sound stimulation output section 10 generates the determined sound stimulations, and thus the sound stimulations determined by the uncomfortable sound pressure determination apparatus 1 are presented to the user 5.

Moreover, from event-related potentials which are cut out based on the sound stimulations of first to $n^{th}$ sounds as starting points, the uncomfortable sound pressure determination apparatus 1 extracts characteristic amounts for estimating the uncomfortable sound pressure, and based on the pattern of characteristic amount variation against changing sound pressure, determines an uncomfortable sound pressure for the right or left ear and for each different frequency.

Figure 13:
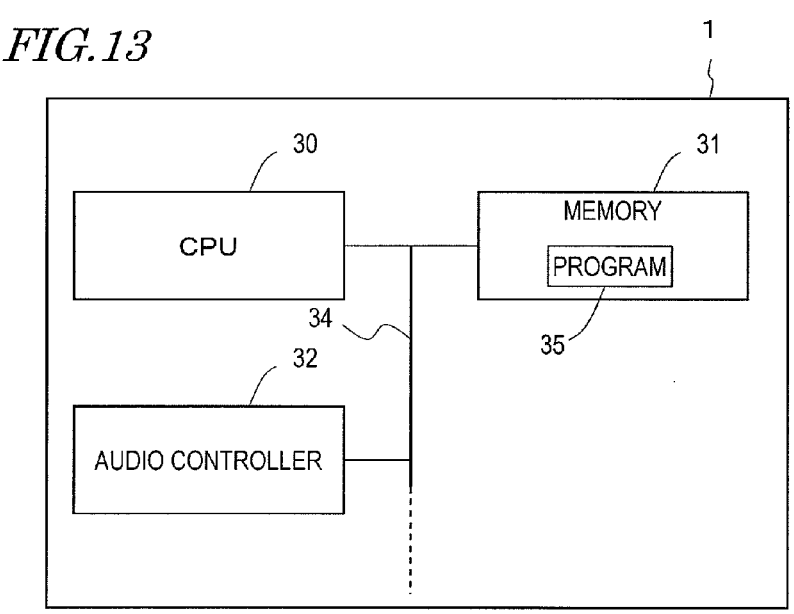
FIG. 13 shows the hardware construction of an uncomfortable sound pressure determination apparatus 1 according to an exemplary embodiment.

FIG. 13 shows the hardware construction of the uncomfortable sound pressure determination apparatus 1 according to the present embodiment. The uncomfortable sound pressure determination apparatus 1 includes a CPU 30, a memory 31, and an audio controller 32. The CPU 30, the memory 31, and the audio controller 32, are interconnected via a bus 34, so that data exchange among them is possible.

The CPU 30 executes a computer program 35 which is stored in the memory 31. A processing procedure as illustrated by a subsequently-described flowchart is described in the computer program 35. In accordance with the computer program 35, the uncomfortable sound pressure determination apparatus 1 performs processes of controlling the entire uncomfortable sound pressure determination system 100, such as generation of sound stimulations, extraction of characteristic amounts of event-related potentials, and analysis when determining an uncomfortable sound pressure. These processes will be described in detail later.

In accordance with instructions from the CPU 30, the audio controller 32 outputs the sound stimulations for presentation via the sound stimulation output section 10 at designated sound pressures.

Note that the uncomfortable sound pressure determination apparatus 1 may be implemented as a piece of hardware (e.g., a DSP) consisting of a semiconductor circuit having a computer program incorporated therein. Such a DSP can realize all functions of the aforementioned CPU 30, memory 31, and audio controller 32 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 13 (e.g., a PC) is able to function as the uncomfortable sound pressure determination apparatus 1 according to the present embodiment.

Figures 14, 15:
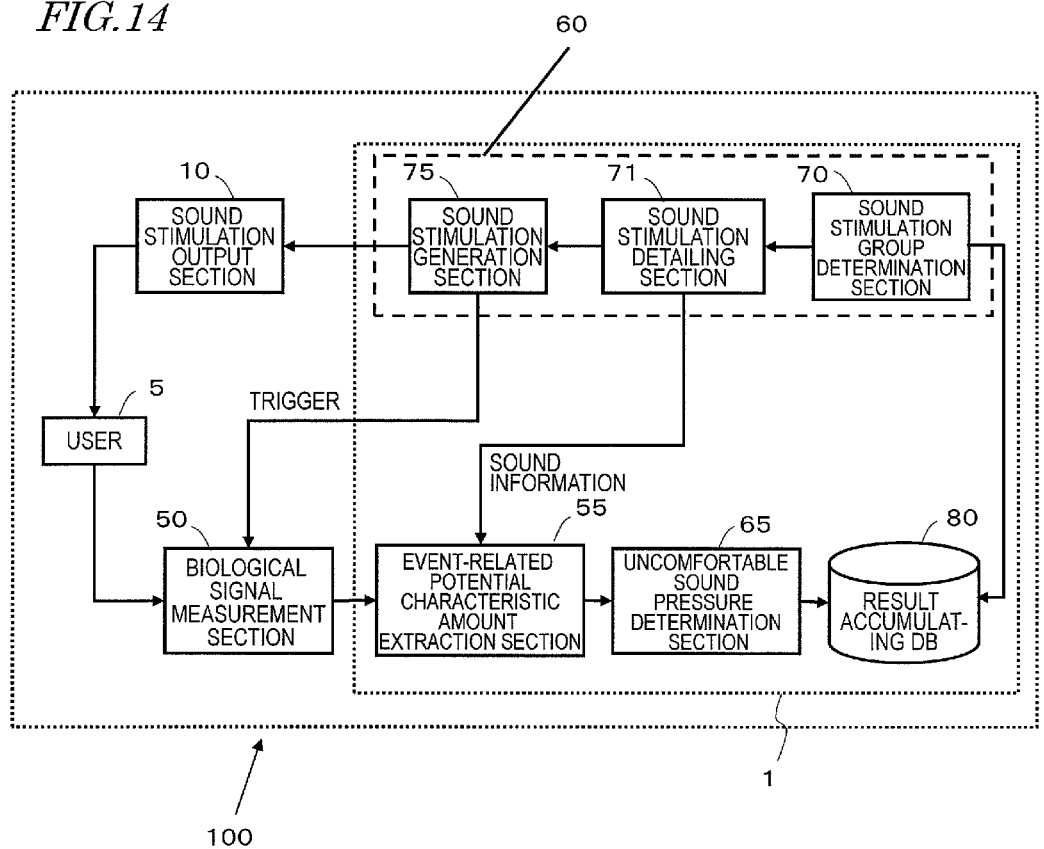
FIG. 14 is a diagram showing the functional block construction of an uncomfortable sound pressure determination system 100 according to an exemplary embodiment.
FIG. 15 is a diagram showing an example of data accumulation in a result accumulating DB 80.

FIG. 14 shows the functional block construction of the uncomfortable sound pressure determination system 100 according to the present embodiment. The uncomfortable sound pressure determination system 100 includes the sound stimulation output section 10, the biological signal measurement section 50, and the uncomfortable sound pressure determination apparatus 1. The uncomfortable sound pressure determination apparatus 1 includes an event-related potential characteristic amount extraction section 55, a sound data generation section 60, an uncomfortable sound pressure determination section 65, and a result accumulating DB 80. The sound data generation section 60 includes a sound stimulation group determination section 70, a sound stimulation detailing section 71, and a sound stimulation generation section 75. The user 5 block is illustrated for ease of explanation. The uncomfortable sound pressure determination apparatus 1 is connected in a wired or wireless manner to the sound stimulation output section 10 and the biological signal measurement section 50.

The respective functional blocks of the uncomfortable sound pressure determination apparatus 1 correspond to functions which are realized by the CPU 30, the memory 31, and the audio controller 32 as a whole upon executing the program which has been described in conjunction with FIG. 13.

The sound data generation section 60 generates a plurality of sounds, which monotonously ascend or monotonously descend from first to $n^{th}$ sounds (n: an integer of two or more). Each of the plurality of sounds is a pure tones of the same frequency. In the present specification, any sounds that have frequencies not different enough to be aurally distinguishable by the user 5 will be regarded as sharing the same frequency. These functions are realized by the sound stimulation group determination section 70, the sound stimulation detailing section 71, and the sound stimulation generation section 75 composing the sound data generation section 60.

The sound stimulation group determination section 70 determines the information of a sound to be presented to the user 5. The sound information includes which of the right or left ear of the user 5 the sound is to be presented to, and the frequency of the presented sound. The ear (right/left) and frequency are determined for each sound stimulation group to be presented. For example, these may be randomly determined under the following constraints: no sound stimulation of the same frequency as that of an immediately previous sound stimulation group is selected; the ear is selected in random order between right and left; however, not more than four sound stimulation groups are successively presented to either the right or left ear. As a result, the influence of taming (habituation) of the electroencephalogram due to successive presentation of sound stimulation groups to the same ear and with the same frequency is reduced, whereby uncomfortable sound pressure determination can be realized with a high precision. Then, the sound stimulation group determination section 70 sends the information of the determined sound stimulation group to the sound stimulation detailing section 71.

The sound stimulation detailing section 71 receives the information concerning the right or left ear and frequency for the sound stimulation group from the sound stimulation group determination section 70. The sound stimulation detailing section 71 determines the particulars of the sound stimulations in the sound stimulation group. "Particulars of the sound stimulations" include the number of sound stimulations, the sound pressures of the first to $n^{th}$ sounds, and the duration of each sound stimulation and the interval between sound stimulations (e.g., 300 ms (ISI1) in FIG. 2) within the sound stimulation group. This will now be specifically described. First, the sound stimulation detailing section 71 determines the number of sound stimulations to be an integer of two or more.

Next, the sound stimulation detailing section 71 determines a sound pressure for each sound stimulation in the number of sound stimulations determined. The respective sound pressures of the sound stimulations are varied in a stepwise manner so that they monotonously ascend or monotonously descend from first to $n^{th}$ sounds. For example, the sound pressures are consecutively varied so that the sound pressure of the second sound is set 5 db larger (or smaller) than the sound pressure of the first sound; the sound pressure of the third sound is set 5 db larger (or smaller) than the sound pressure of the second sound; and so on. The changes in sound pressure may be constant or different, so long as the sound pressure is monotonously ascending or monotonously descending. In accordance with the level of hypacusia, the sound pressures are to be determined so that an uncomfortable sound pressure is expected to exist within the range, and that they are least harmful to the ears. For example, in the case where the number of sound stimulations is three, and the person has an intermediate level of hypacusia, the first to third sounds may be set to 90 dBSPL, 95 dBSL, and 100 dBSPL, respectively. Moreover, the sound stimulation detailing section 71 determines durations and timings with which to present the sound stimulations. The duration is set to e.g. 25 ms or more, so as to stably induce an auditory evoked potential. The sound stimulation interval is set to a time which is equal to or greater than the duration of each sound stimulation and which is 1 second or less. For example, the sound stimulation interval may be no less than 100 ms and no more than 1 s. Since it suffices if a P2 component which is induced around 200 ms after the presentation of a stimulation is available, the sound stimulation interval may be no less than 200 ms and no more than 1 s, for example. With a predetermined timing, the sound stimulation detailing section 71 sends the determined number of sound stimulations, sound pressure, duration, and sound stimulation interval, and the information of right or left ear and frequency having been received from the sound stimulation group determination section 70, to the sound stimulation generation section 75 and the event-related potential characteristic amount extraction section (hereinafter "extraction section") 55.

Based on the information of right or left ear, frequency, number of sound stimulations, sound pressure, duration, and sound stimulation interval received from the sound stimulation detailing section 71, the sound stimulation generation section 75 generates sound stimulation data. An example of each sound stimulation may be a tone burst sound with a rise and fall of 3 ms. The sound stimulation generation section 75 outputs a sound stimulation to the user via the sound stimulation output section 10, and at that timing outputs a trigger signal to the biological signal measurement section 50. The sound stimulation data may be generated in such a manner that a single piece of sound stimulation data is created for one sound stimulation group, from which a plurality of sound stimulations that undergo changes in sound pressure at a predetermined time interval are derived, for example. In that case, the trigger signal to be sent to the biological signal measurement section 50 may only be sent at the timing of presenting the first sound.

The sound stimulation output section 10 reproduces the sound stimulation data which has been generated by the sound stimulation generation section 75, for output to the user 5.

The biological signal measurement section 50, which is an electroencephalograph for measuring a biological signal of the user 5, measures an electroencephalogram as the biological signal. Based on a trigger received from the sound stimulation generation section 75 as a starting point, the biological signal measurement section 50 cuts out event-related potentials in a predetermined zone (e.g., a zone from 100 ms before presentation of the first sound to 400 ms after presentation of the $n^{th}$ sound), and sends that waveform data (event-related potential) to the extraction section 55.

An event-related potential is a potential fluctuation of an electroencephalogram which occurs in response to a stimulation. An event-related potential may be of different types as to, for example:

(1) polarity of potential (plus or minus);
(2) latency (the amount of time after a stimulation is generated until a potential fluctuation occurs); and
(3) amplitude level of potential.

Each different type of signal contains different information concerning the user 5. Note that a measured electroencephalogram may be subjected to frequency filtering with a cutoff frequency which is appropriate for the electroencephalogram data. An event-related potential may be cut out from an electroencephalogram which has been subjected to such frequency filtering. In the case where a band-pass filter is used as the frequency filter, its cutoff frequency may be set so as to pass an event-related potential of e.g. 5 Hz to 15 Hz. It is assumed that the user 5 has already put on the electroencephalograph. The probe electrode for electroencephalogram measurement is attached at the central portion Cz, for example.

From the event-related potential received from the biological signal measurement section 50, in accordance with the particulars of the sound stimulations received from the sound stimulation detailing section 71, the extraction section 55 calculates temporal change information concerning the frequency of the event-related potential with respect to each of the first to $n^{th}$ sounds (where n is an integer of two or more). An example of temporal change information of event-related potential frequency may be a characteristic amount related to a wavelet coefficient(s) (hereinafter referred to as a "wavelet-coefficient related characteristic amount"). The calculated characteristic amount and the sound stimulation information (right or left ear, frequency, sound pressure, etc.) are sent to the uncomfortable sound pressure determination section 65. The wavelet-coefficient related characteristic amount may be derived as an average value over a predetermined range on each of the frequency axis and the time axis, for example. For instance, an average may be taken over a range from 5 to 15 Hz on the frequency axis and over a time range of 50 ms on the time axis. The ranges on the frequency axis and the time axis over which averaging is to be conducted for characteristic amount calculation may be finer or coarser than from 5 to 15 Hz and every 50 ms, respectively.

Based on the temporal change information of event-related potential frequency, the uncomfortable sound pressure determination section 65 determines an uncomfortable sound pressure. More specifically, the uncomfortable sound pressure determination section 65 determines an uncomfortable sound pressure in view of the wavelet-coefficient related characteristic amounts in response to the first to $n^{th}$ sounds that have been received from the extraction section 55. The uncomfortable sound pressure determination section 65 performs linear discrimination by utilizing previously-provided training data on wavelet characteristic amounts and subjective UCL values. The training data is generated from subjective UCL values and wavelet characteristic amounts which were determined through a subjective report experiment and electroencephalogram measurement experiment as described above, the subjective report experiment and electroencephalogram measurement experiment being previously conducted for at least two or more other people. Herein, the sound stimulation conditions concerning the sound pressure and number of sound stimulations in the electroencephalogram measurement experiment performed when generating the training data need to identically conform to the pattern of changing stimulation sound pressure as determined by the sound stimulation detailing section 71. The retaining training data may be retained so as to be itemized for the right or left ear and for each different frequency, as shown in FIG. 8, for example. In that case, based on the sound stimulation information of right or left ear and frequency received from the extraction section 55, the training data which is utilized for uncomfortable sound pressure determination may be switched as appropriate, so that the right or left ear and frequency of the training data match those of the person who is the subject of determination. Moreover, the training data may be switched according to the user's symptoms of hypacusia. For example, it may be switched between general categories, e.g., conductive deafness and perceptive deafness, or switched according to the audiogram pattern, e.g., gradual low tone loss or gradual high tone loss. The uncomfortable sound pressure determination section 65 sends the determined uncomfortable sound pressure to the result accumulating DB 80.

The result accumulating DB 80 stores the uncomfortable sound pressure received from the uncomfortable sound pressure determination section 65 in association with the right or left ear and each frequency as indicated by the sound stimulation group information received from the sound stimulation group determination section 70.

FIG. 15 shows an example of data accumulation in the result accumulating DB 80. FIG. 15 illustrates a case where an uncomfortable sound pressure is accumulated with respect to each of the right or left ear and each different frequency (unit: dBHL).

Figure 16:
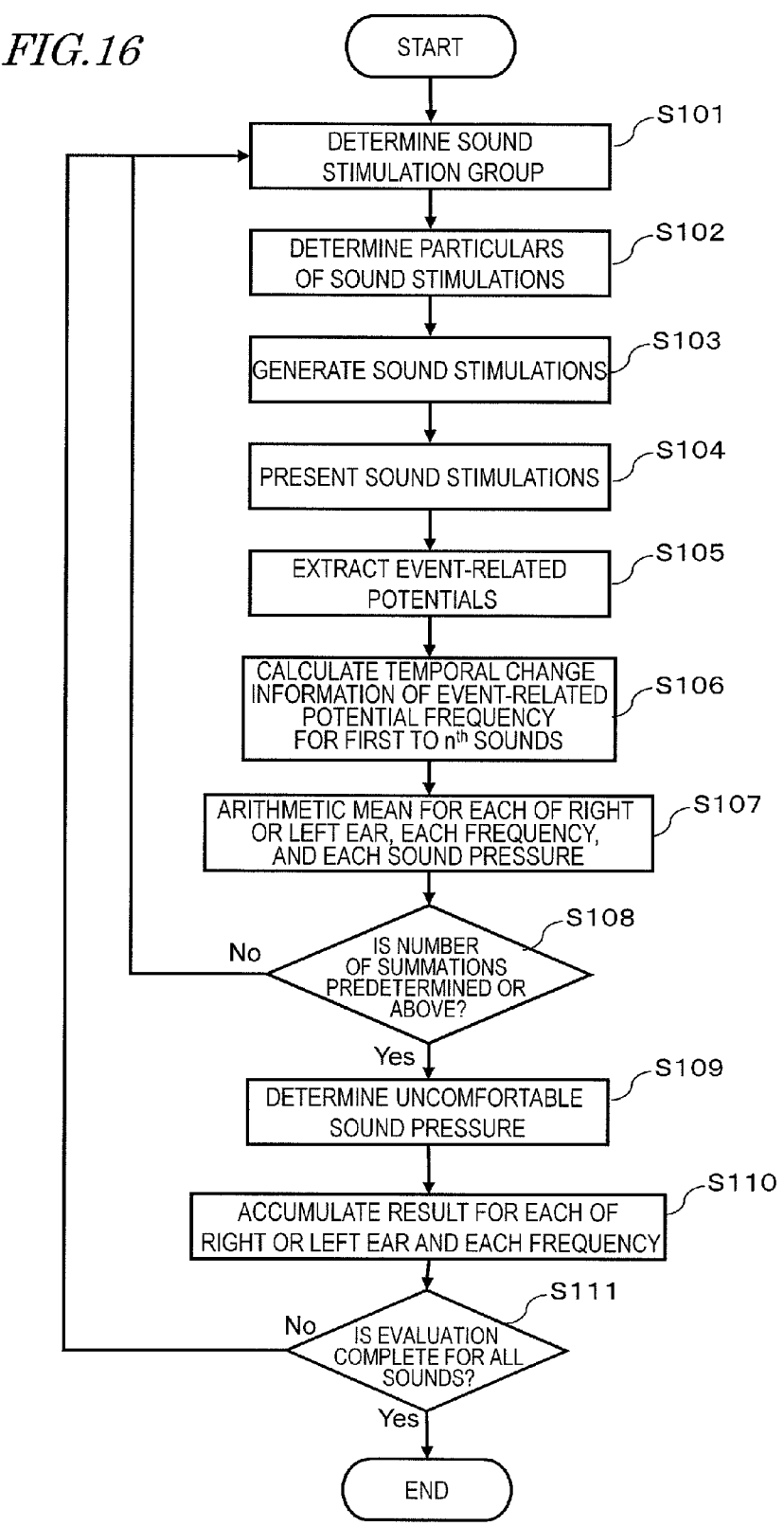
FIG. 16 is a flowchart showing a procedure of processing performed in the uncomfortable sound pressure determination system 100.

Next, with reference to FIG. 16, a processing procedure which is performed by the uncomfortable sound pressure determination system 100 of FIG. 14 will be described. FIG. 16 is a flowchart showing a procedure of processing performed in the uncomfortable sound pressure determination system 100.

At step S101, the sound stimulation group determination section 70 determines the right or left ear and frequency for a sound stimulation group to be presented. For example, these may be randomly determined under the following constraints: no sound stimulation of the same frequency as that of an immediately previous sound stimulation group is selected; the ear is selected in random order between right and left; however, not more than four sound stimulation groups are successively presented to either the right or left ear.

At step S102, from the sound stimulation group determination section 70, the sound stimulation detailing section 71 receives information concerning the right or left ear and frequency for the sound stimulation group, and as the particulars of the sound stimulations in the sound stimulation group, determines the number of sound stimulations, the sound pressures of the first to $n^{th}$ sounds, and the duration of each sound stimulation and the interval between sound stimulations within the sound stimulation group.

At step S103, based on the sound stimulation information received from the sound stimulation detailing section 71, the sound stimulation generation section 75 generates sound stimulation data. An example of each sound stimulation may be a tone burst sound with a rise and fall of 3 ms.

At step S104, the sound stimulation generation section 75 outputs each sound stimulation to the user via the sound stimulation output section 10, and at that timing outputs a trigger signal to the biological signal measurement section 50. The sound stimulation data may be generated in such a manner that a single piece of sound stimulation data is created for one sound stimulation group, from which a plurality of sound stimulations that undergo changes in sound pressure at a predetermined time interval are derived, for example. In that case, the trigger signal to be sent to the biological signal measurement section 50 may only be sent at the timing of presenting the first sound.

At step S105, the biological signal measurement section 50 measures an electroencephalogram as the biological signal. Then, the biological signal measurement section 50 applies frequency filtering with an appropriate cutoff frequency to the electroencephalogram data, and based on a trigger received from the sound stimulation generation section 75 as a starting point, cuts out event-related potentials in a predetermined zone (e.g., a zone from 100 ms before presentation of the first sound to 400 ms after presentation of the $n^{th}$ sound), and sends that waveform data (event-related potential) to the extraction section 55.

At step S106, from the event-related potential received from the biological signal measurement section 50, in accordance with the particulars of the sound stimulations received from the sound stimulation detailing section 71, the extraction section 55 calculates temporal change information concerning the frequency (which in one example may be a wavelet-coefficient related characteristic amount) of each of the event-related potentials in response to the first to $n^{th}$ sounds.

The extraction section 55 applies a continuous wavelet transform to an event-related potential waveform in a range from 0 ms to 300 ms based on the point of presenting each of the first to $n^{th}$ sounds as a starting point (0 ms), thereby calculating a wavelet coefficient for each time and each frequency. The Mexican hat function may be used as a mother wavelet.

At step 107, based on the sound stimulation information received from the sound stimulation detailing section 71, the extraction section 55 takes an arithmetic mean of the information (which in one example may be wavelet-coefficient related characteristic amounts) calculated at step S106, for each frequency. In a manner similar to the aforementioned experiment, an arithmetic mean is taken of the waveforms and wavelet coefficients of event-related potentials for each condition and for each sound stimulation group of first to fifth sounds. The waveforms and wavelet coefficients of event-related potentials are to be arithmetic-meaned at least for each frequency. Note that, the waveforms and wavelet coefficients of event-related potentials may be arithmetic-meaned for each individual person and for each of the right or left ear. Those trials which exhibit an amplitude in absolute value of 50 µV or more at any electrode are excluded from the total arithmetic mean and arithmetic mean, because they presumably are under the influence of noises, e.g., eye movements and blinks. Then, as a characteristic amount of the event-related potential potentially serving as an index of uncomfortable sound pressure, an average value of the arithmetic mean wavelet coefficients in a frequency range from 5 Hz to 15 Hz is calculated in a time range of every 50 ms, and used as the characteristic amount. This characteristic amount may also be referred to as a wavelet characteristic amount.

At step S108, the extraction section 55 determines whether the number of summations (in the arithmetic mean) for the sound stimulations in the sound stimulation group presented at step S104 has reached a predetermined number of times. If the number of summations is less than the predetermined number of times, the process returns to step S101 to repeat presentation of the sound stimulation group. If the number of summations is equal to greater than the predetermined number of times, the extraction section 55 sends the arithmetic-meaned wavelet-coefficient related characteristic amount to the uncomfortable sound pressure determination section 65, and the process proceeds to step S109. The predetermined number of times may be 20 times, for example. Note that "20 times" is a mere example, although it is a number of summations which is frequently adopted in fields where event-related potentials are to be measured.

At step S109, the uncomfortable sound pressure determination section 65 determines an uncomfortable sound pressure in view of the wavelet-coefficient related characteristic amounts in response to the first to $n^{th}$ sounds that have been received from the extraction section 55. The uncomfortable sound pressure determination is realized through linear discrimination by utilizing previously-provided training data on wavelet characteristic amounts and subjective UCL values of other people.

At step S110, the result accumulating DB 80 accumulates the information of a result of uncomfortable sound pressure determination that is received from the uncomfortable sound pressure determination section 65 for each of the right or left ear and for each frequency of the sound stimulation group presented at step S104.

At step S111, the sound stimulation group determination section 70 determines whether presentation has been completed for all of the sound stimulations to be subjected to uncomfortable sound pressure determination. If it is not completed, the process returns to step S101; if it is completed, the uncomfortable sound pressure determination is ended.

The uncomfortable sound pressure determination system 100 of the present embodiment presents pure tones of the same frequency totaling n times (where n is an integer of two or more) at monotonously ascending or monotonously descending sound pressures. The uncomfortable sound pressure determination system 100 extracts electroencephalographic characteristic amounts in response to the respective sound stimulations of first to $n^{th}$ sounds, and determines an uncomfortable sound pressure by using a change pattern of the characteristic amounts in response to the plurality of sound stimulations. This realizes a hearing aid fitting such that the user will not experience an uncomfortable sound pressure when wearing a hearing aid.

A change pattern of characteristic amounts provides a relationship by which characteristic amounts of event-related potentials in response to a plurality of sounds can be associated with an uncomfortable sound pressure. FIG. 8 shows an example of a relationship by which characteristic amounts of the event-related potentials in response to first to fifth sounds and subjective UCL values corresponding to predetermined uncomfortable sound pressures are associated. For each frequency, the relationship between characteristic amounts of event-related potentials in response to a plurality of sounds and an uncomfortable sound pressure is defined by a change pattern of characteristic amounts.

If suffices so long as characteristic amounts of event-related potentials in response to any plural number of sounds are used. For example, these may be event-related potentials in response to the first and second sounds, in which case the relationship should define an association between a characteristic amount of the event-related potential in response to the first sound and a characteristic amount of the event-related potential in response to the second sound, and an uncomfortable sound pressure. It may be any other combination, e.g., event-related potentials in response to the first and third sounds.

In the present embodiment, it is illustrated that the biological signal measurement section 50 cuts out an event-related potential in a predetermined range based on a trigger from the sound stimulation generation section 75 as a starting point, and sends it to the extraction section 55. However, this process is an example. In another process, for example, the biological signal measurement section 50 may constantly measure an electroencephalogram, and the extraction section 55 may perform cutting out of an event-related potential and a baseline correction as needed. With such a construction, the sound stimulation generation section 75 does not need to send a trigger to the biological signal measurement section 50, but may only send a trigger to the extraction section 55.

Although the present embodiment illustrates that the uncomfortable sound pressure determination results are accumulated in the result accumulating DB 80, accumulation is not necessary. For example, in the case where the result accumulating DB 80 is provided external to the uncomfortable sound pressure determination apparatus 1, each result of determination of the uncomfortable sound pressure determination section 65 may simply be output. Each result of determination can be utilized as information concerning uncomfortable sound pressure.

Figure 17:
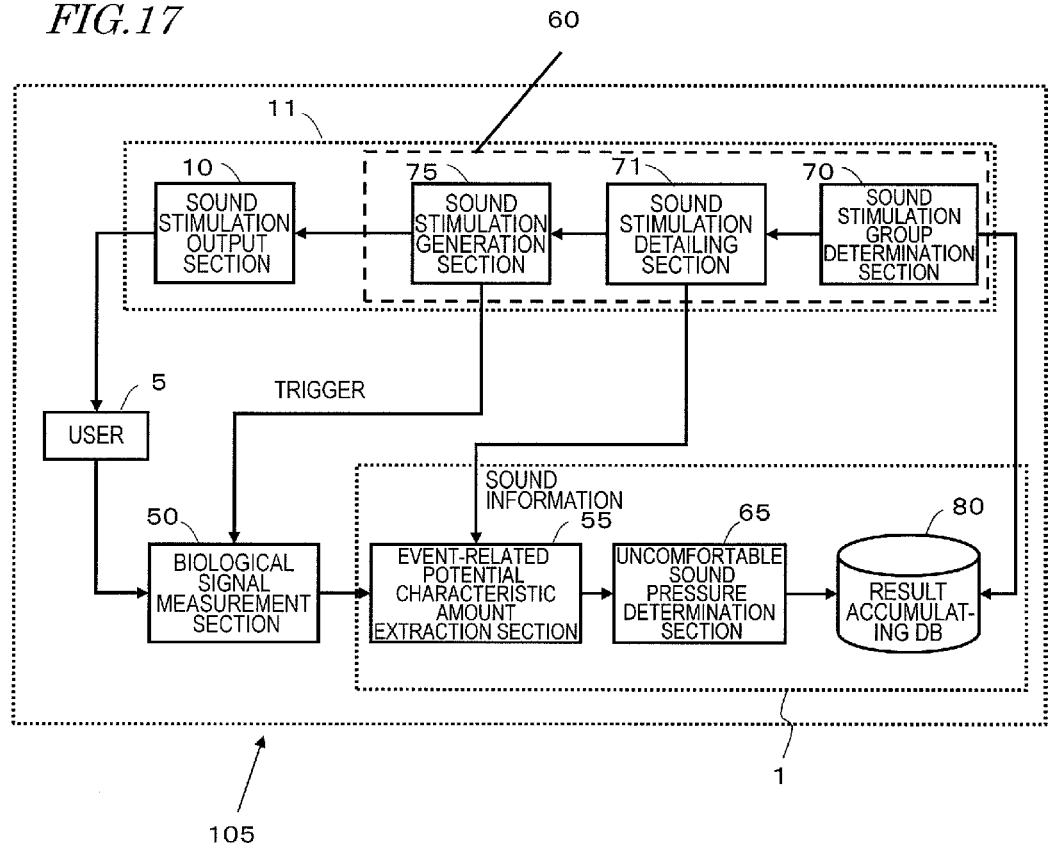
FIG. 17 is a diagram showing the construction of an uncomfortable sound pressure evaluation system 105, as a variant of the uncomfortable sound pressure evaluation system 100 (FIG. 14).

FIG. 17 shows the construction of an uncomfortable sound pressure evaluation system 105, as a variant of the uncomfortable sound pressure evaluation system 100 (FIG. 14). The uncomfortable sound pressure evaluation system 105 includes the uncomfortable sound pressure determination apparatus 1, a sound stimulation apparatus 11, and a biological signal measurement section 50, which are interconnected in a wired or wireless manner for exchanging of information. The sound stimulation apparatus 11 has combined functions of the sound data generation section 60 (sound stimulation group determination section 70, sound stimulation detailing section 71, sound stimulation generation section 75) and the sound stimulation output section 10.

Other variants are also possible. Those skilled in the art would be able to implement an apparatus or circuit in which one or more component elements described above are combined.

Note that the characteristic amount is not limited only to the wavelet coefficient and the N1-P2 amplitude. A characteristic feature of an event-related potential manifests itself in the waveform shape, and thus is describable in terms of latency (i.e., elapsed time from the timing of presenting a stimulation) and amplitude of a peak that appears. Any form of description of such a characteristic feature that is made in terms of time, frequency, or shape would be available as a characteristic feature for distinction. In the present specification, the wavelet coefficient is an example of information that is indicative of temporal change in the frequency of an event-related potential. Moreover, a machine learning technique such as discriminant analysis or Bayesian estimation may be employed, to which conceivable characteristic amounts may be supplied in vectorial form, whereby the respective parameters will be appropriately weighted. This will eliminate the need to previously narrow down to any one characteristic amount.

Note that this UCL evaluation result is to be used as a piece of information for setting a maximum output value for a hearing aid when "fitting" a hearing aid.

Figure 18:
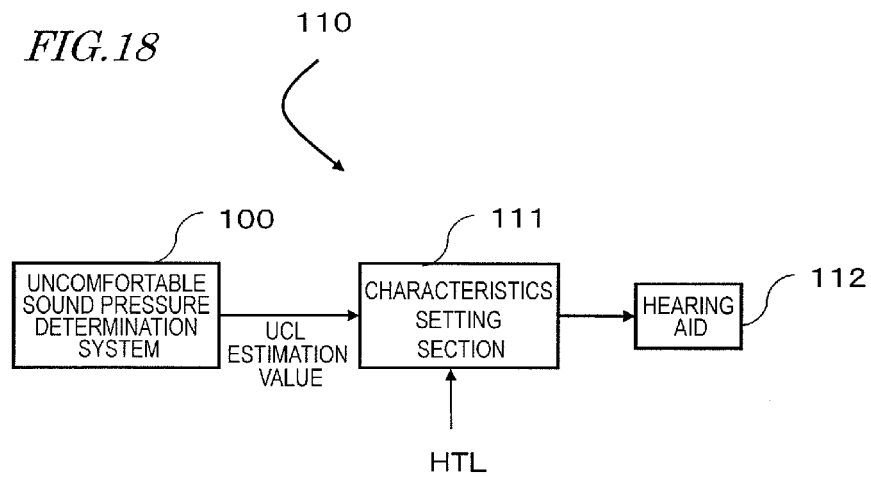
FIG. 18 is a diagram showing the construction of a hearing aid adjustment system 110.

For example, FIG. 18 shows the construction of a hearing aid adjustment system 110. The hearing aid adjustment system 110 includes the uncomfortable sound pressure determination system 100 shown in FIG. 14, as well as a characteristics setting section 111 and a hearing aid 112. Note that the uncomfortable sound pressure determination system 100 is an example. Instead of the uncomfortable sound pressure determination system 100, a hearing aid adjustment system may be constructed by using any variant uncomfortable sound pressure determination system, such as that shown in FIG. 17.

The characteristics setting section 111 receives uncomfortableness threshold values that have been estimated by the uncomfortable sound pressure determination system 100, and hearing threshold levels (HTLs) each indicating a minimum sound pressure of a pure tone that the user 1 is able to hear. The pure tone frequencies may be 1000 Hz, 2000 Hz, and 4000 Hz, for example. A hearing threshold level (HTL) is defined for each frequency. The hearing threshold levels (HTLs) may be sent from a device for measuring the hearing threshold level (audiometer; not shown) in a wired or wireless manner, or via a storage medium, for example. The characteristics setting section 111 sets each uncomfortableness threshold value to the hearing aid 112 as a maximum output value. Moreover, the characteristics setting section 111 may set each hearing threshold level (HTL) as a minimum output value to the hearing aid 112.

The hearing aid adjustment system 110 may at least include the characteristics setting section 111. The characteristics setting section 111 receives the uncomfortable sound pressures having been determined by the uncomfortable sound pressure determination section 65, and sets the characteristics of the hearing aid 112. The uncomfortable sound pressure determination section 65 in this case may not be part of the hearing aid adjustment system 110.

With an uncomfortable sound pressure determination apparatus according to an embodiment of the present disclosure and an uncomfortable sound pressure determination system in which the uncomfortable sound pressure determination apparatus is incorporated, it is possible to objectively determine whether a user feels that a sound pressure is so loud as to be uncomfortable. This realizes a hearing aid fitting which prevents the user from experiencing an uncomfortable sound pressure and which does not induce aural fatigue, and therefore is applicable to the fitting of any and all hearing aid users.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An uncomfortable sound pressure determination system comprising:
    one or more memories; and
    circuitry which in operation is configured to:
    measure an electroencephalogram signal of a user;
    generate sound data concerning a plurality of sounds consecutively ascending or descending in sound pressure from first to $n^{th}$ sounds (n: an integer of two or more), the plurality of sounds being pure tones of a same frequency;
    present the plurality of sounds to the user based on the sound data;
    extract for each of the plurality of sounds, based on an event-related potential of the electroencephalogram signal measured after lapse of a predetermined time from a point in time of presenting each of the plurality of sounds, a characteristic amount concerning temporal change in frequency of the event-related potential; and
    determine, by referring to a previously-provided relationship by which temporal changes in frequency of event-related potentials and uncomfortable sound pressures are associated, a sound pressure corresponding to the extracted characteristic amount to be an uncomfortable sound pressure at the frequency.

2. The uncomfortable sound pressure determination system of claim 1, wherein, the circuitry in operation further is configured to:
    at least determine the frequency of the plurality of sounds;
    at least determine sound pressures of the first to $n^{th}$ sounds; and
    generate sound data concerning a plurality of sounds having the determined frequency and having consecutively ascending or descending determined sound pressures from the first to $n^{th}$ sounds.

3. The uncomfortable sound pressure determination system of claim 2, wherein the circuitry ensures that the sound pressures are ascending or descending by a predetermined difference from the first to $n^{th}$ sounds.

4. The uncomfortable sound pressure determination system of claim 3, wherein the circuitry ensures that the sound pressures are ascending or descending by 5 dB from the first to $n^{th}$ sounds.

5. The uncomfortable sound pressure determination system of claim 3, wherein the circuitry is configured to retain as training data a previously-provided relationship of one or more persons other than the user by which characteristic amounts concerning temporal changes in frequency of event-related potentials and sound pressures are associated, and performs linear discrimination by using the extracted characteristic amount against the training data.

6. The uncomfortable sound pressure determination system of claim 5, wherein,
    the circuitry is configured to determine whether the plurality of sounds are to be presented to a right or left ear; and
    the circuitry is configured to retain a plurality of pieces of said training data, each piece of training data concerning one of a right ear and a left ear and a frequency, and switches between the pieces of training data depending on whether the ear determined is right or left and depending on the frequency.

7. The uncomfortable sound pressure determination system of claim 6, wherein,
    the characteristic amount concerning temporal change in frequency of the event-related potential is a wavelet-coefficient related characteristic amount; and
    the circuitry is configured to extract the wavelet-coefficient related characteristic amount based on an event-related potential of the electroencephalogram signal measured at a point in time not later than 300 ms from a point in time of presenting each of the plurality of sounds.

8. The uncomfortable sound pressure determination system of claim 7, wherein the circuitry is configured to extract as the characteristic amount a value obtained by averaging wavelet coefficients of the event-related potential over a predetermined frequency range and a predetermined time range.

9. The uncomfortable sound pressure determination system of claim 8, wherein the predetermined frequency range is no less than 5 Hz and no more than 15 Hz.

10. The uncomfortable sound pressure determination system of claim 8, wherein the predetermined time range is 50 ms.

11. The uncomfortable sound pressure determination system of claim 8, wherein the circuitry is configured to determine the uncomfortable sound pressure by using the characteristic amounts in response to the first sound and the second sound.

12. The uncomfortable sound pressure determination system of claim 6, wherein the one or more memories stores a database in which uncomfortable sound pressures at the frequency are to be accumulated, the uncomfortable sound pressures being determined by the circuitry.

13. The uncomfortable sound pressure determination system of claim 12, wherein the database accumulates an uncomfortable sound pressure for each of the right or left ear and for each frequency.

14. The uncomfortable sound pressure determination system of claim 12, wherein,
    the circuitry that performs the biological signal measurement,
    a sound stimulation apparatus having the circuitry that performs the sound data generation and the output, an uncomfortable sound pressure determination apparatus having the circuitry that performs the characteristic amount extraction and, the uncomfortable sound pressure determination, and the one or more memories storing the database are interconnected.

15. A hearing aid adjustment system comprising circuitry configured to receive the uncomfortable sound pressure estimated by using the uncomfortable sound pressure determination system of claim 1, and setting the uncomfortable sound pressure to a hearing aid as a maximum output value.

16. An uncomfortable sound pressure determination apparatus comprising:
one or more memories; and
circuitry which in operation is configured to:
extract a characteristic amount concerning temporal change in frequency of an event-related potential, when a plurality of sounds output from an output section are presented to a user, the plurality of sounds consecutively ascending or descending in sound pressure from first to $n^{th}$ sounds (n: an integer of two or more), for each of the plurality of sounds based on the event-related potential of an electroencephalogram signal of the user measured by an electroencephalograph after lapse of a predetermined time from a point in time of presenting each of the plurality of sounds; and
determine, by referring to a previously-provided relationship by which temporal changes in frequency of event-related potentials and uncomfortable sound pressures are associated, a sound pressure corresponding to the extracted characteristic amount to be an uncomfortable sound pressure at the frequency.

17. An uncomfortable sound pressure determination method, comprising the steps of:
measuring an electroencephalogram signal of a user;
generating sound data concerning a plurality of sounds consecutively ascending or descending in sound pressure from first to $n^{th}$ sounds (n: an integer of two or more), the plurality of sounds being pure tones of a same frequency;
presenting the plurality of sounds to the user based on the sound data;
extracting for each of the plurality of sounds, based on an event-related potential of the electroencephalogram signal measured after lapse of a predetermined time from a point in time of presenting each of the plurality of sounds, a characteristic amount concerning temporal change in frequency of the event-related potential; and
determining, by referring to a previously-provided relationship by which temporal changes in frequency of event-related potentials and uncomfortable sound pressures are associated, a sound pressure corresponding to the characteristic amount extracted by the extracting step to be an uncomfortable sound pressure at the frequency.

18. A non-transitory computer-readable medium storing a computer program to be executed by a computer mounted in an uncomfortable sound pressure determination apparatus of an uncomfortable sound pressure determination system,
wherein the computer program causes the computer to execute the steps of:
acquiring an electroencephalogram signal of a user;
generating sound data concerning a plurality of sounds consecutively ascending or descending in sound pressure from first to $n^{th}$ sounds (n: an integer of two or more), the plurality of sounds being pure tones of a same frequency;
presenting the plurality of sounds to the user based on the sound data via an output section;
extracting for each of the plurality of sounds, based on an event-related potential of the electroencephalogram signal measured after lapse of a predetermined time from a point in time of presenting each of the plurality of sounds, a characteristic amount concerning temporal change in frequency of the event-related potential; and
determining, by referring to a previously-provided relationship by which temporal changes in frequency of event-related potentials and uncomfortable sound pressures are associated, a sound pressure corresponding to the characteristic amount extracted by the extracting step to be an uncomfortable sound pressure at the frequency.

* * * * *